United States Patent
Perrior et al.

(10) Patent No.: US 8,962,609 B2
(45) Date of Patent: Feb. 24, 2015

(54) PYRIMIDINE COMPOUNDS AS INHIBITORS OF PROTEIN KINASES IKK EPSILON AND/OR TBK-1, PROCESSES FOR THEIR PREPARATION, AND PHARMACEUTICAL COMPOSITIONS CONTAINING THEM

(75) Inventors: Trevor Robert Perrior, Cambridge (GB); Gary Karl Newton, Cambridge (GB); Mark Richard Stewart, Cambridge (GB); Rehan Aqil, Cambridge (GB)

(73) Assignee: Domainex Limited (GB)

( * ) Notice: Subject to any disclaimer, the term of this patent is extended or adjusted under 35 U.S.C. 154(b) by 242 days.

(21) Appl. No.: 13/811,164

(22) PCT Filed: Jul. 18, 2011

(86) PCT No.: PCT/GB2011/001075
§ 371 (c)(1),
(2), (4) Date: Mar. 5, 2013

(87) PCT Pub. No.: WO2012/010826
PCT Pub. Date: Jan. 26, 2012

(65) Prior Publication Data
US 2013/0267491 A1  Oct. 10, 2013

(30) Foreign Application Priority Data
Jul. 19, 2010  (GB) .................................. 1012105.1

(51) Int. Cl.
| | | |
|---|---|---|
| A61K 31/5377 | (2006.01) | |
| A61K 31/535 | (2006.01) | |
| A61K 31/497 | (2006.01) | |
| A61K 31/505 | (2006.01) | |
| C07D 401/12 | (2006.01) | |
| C07D 401/14 | (2006.01) | |
| C07D 413/14 | (2006.01) | |
| C07D 403/10 | (2006.01) | |
| C07D 417/10 | (2006.01) | |
| C07D 403/14 | (2006.01) | |
| C07D 239/42 | (2006.01) | |
| C07D 403/12 | (2006.01) | |
| C07D 417/14 | (2006.01) | |

(52) U.S. Cl.
CPC ............ *C07D 403/10* (2013.01); *C07D 239/42* (2013.01); *C07D 401/12* (2013.01); *C07D 401/14* (2013.01); *C07D 403/12* (2013.01); *C07D 403/14* (2013.01); *C07D 413/14* (2013.01); *C07D 417/14* (2013.01)
USPC ................ 514/210.2; 514/235.8; 514/252.18; 514/275; 544/122; 544/295; 544/331; 544/332

(58) Field of Classification Search
CPC .. C07D 401/12; C07D 401/14; C07D 413/14; C07D 403/10; C07D 417/10; C07D 403/14

USPC ...................... 514/210.2, 235.8, 252.18, 275; 544/122, 295, 331, 332
See application file for complete search history.

(56) References Cited

U.S. PATENT DOCUMENTS

| | | |
|---|---|---|
| 2003/0203926 A1 | 10/2003 | Kois et al. |
| 2003/0220330 A1 | 11/2003 | Yoshitaka et al. |
| 2004/0106634 A1 | 6/2004 | Satoh et al. |
| 2006/0079543 A1 | 4/2006 | Sum et al. |
| 2007/0244140 A1 | 10/2007 | Hu et al. |
| 2009/0048282 A1 | 2/2009 | Hauze et al. |
| 2010/0069417 A1 | 3/2010 | Bouaboula et al. |

FOREIGN PATENT DOCUMENTS

| | | |
|---|---|---|
| CN | 101600697 A | 12/2009 |
| WO | 02/102313 A2 | 12/2002 |
| WO | 2005/012262 A1 | 2/2005 |
| WO | 2005/012262 * | 10/2005 |
| WO | 2007/089768 A2 | 8/2007 |
| WO | 2008/109943 A1 | 9/2008 |
| WO | 2008/124085 A2 | 10/2008 |
| WO | 2009/032861 A1 | 3/2009 |
| WO | 2011/046970 A1 | 4/2011 |
| WO | 2012/142329 A1 | 10/2012 |

OTHER PUBLICATIONS

PCT/GB2011/001075 International Search Report and Written Opinion dated Jan. 31, 2013.

* cited by examiner

*Primary Examiner* — James O Wilson
*Assistant Examiner* — Ebenezer O Sackey
(74) *Attorney, Agent, or Firm* — Hahn Loeser & Parks LLP

(57) ABSTRACT

C Compounds of the general formula (I) and salts thereof are useful in the treatment of diseases associated with aberrant activity of the protein kinases IKKε and/or TBK-1: in which: $R^1$ represents an aliphatic heterocyclyl group having 4, 5, 6 or 7 ring atoms, bonded to the phenyl group shown in formula I through a ring nitrogen atom, and optionally substituted by one or more substituents defined in the Specification; $R^2$ represents a phenyl or heteroaryl group which is optionally substituted by one or more substituents defined in the Specification; and each of $R^3$ and $R^4$ independently represents a hydrogen atom or a $C_{1-4}$ alkyl group.

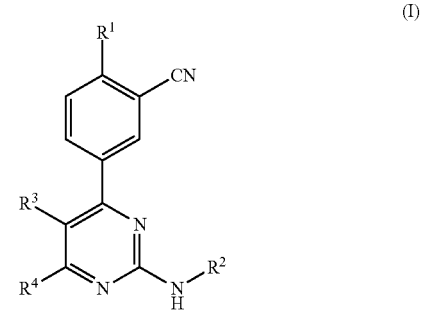

21 Claims, No Drawings

PYRIMIDINE COMPOUNDS AS INHIBITORS OF PROTEIN KINASES IKK EPSILON AND/OR TBK-1, PROCESSES FOR THEIR PREPARATION, AND PHARMACEUTICAL COMPOSITIONS CONTAINING THEM

The present invention relates to novel pyrimidine compounds and compositions containing them, and to processes for preparing them. The compounds are useful in the treatment of diseases associated with aberrant activity of the protein kinases IKKε and/or TBK-1.

An important large family of enzymes is the protein kinase family. There are approximately 500 different known protein kinases. Protein kinases serve to catalyze the phosphorylation of an amino acid side chain in various substrate proteins. I-kappa-B-kinase epsilon, IKKε, (also known as I-kappa-B-kinase-3 (IKK3) or inducible I-kappa-B-kinase (IKKi)), and TANK Binding Kinase-1, TBK-1 (also known as T2K or NF-kappa B-activating kinase), are serine-threonine kinases. Studies have shown that protein kinases play a key role in many cell functions, including signal transduction, transcriptional regulation, cell motility, and cell division. Aberrant or inappropriate protein kinase activity can contribute to the development and maintenance of certain disease states. Several oncogenes have also been shown to encode protein kinases, suggesting that kinases play a role in oncogenesis IKKε is not believed to be a component of the "classical" IKK pathway for the activation of transcription factors such as the NF-κB family in which its homologues IKKα and IKKβ are known to have a key role. However it has been shown to take part in an alternative mechanism for the regulation of transcription factors such as the NF-κB family and interferon-regulatory factor 3 (IRF3), all of which are known to be involved in controlling the expression of a number of regulatory proteins including pro-inflammatory cytokines. IKKε directly phosphorylates the C-terminal domain of the NF-κB family member cRel, leading to dissociation of the IkBα-cRel complex and thereby allowing nuclear accumulation of cRel.

Aberrant IKKε activity has been linked to a number of disease areas including cancer and obesity. Studies have shown that the gene encoding IKKε (IKBE) is amplified and over expressed in certain breast cancer cell lines and patient derived tumours. Furthermore suppression of IKBE gene expression in these cell lines induces cell death (Boehm et al., *Cell,* 2007, 129, 1065-1079). IKKε has also been shown to phosphorylate the estrogen receptor, and its activity has been linked to tamoxifen resistance in breast cancer tumours (Guo et al., *The Journal of Biological Chemistry,* 2010, 285, 3676-3684). IKKε is also frequently over expressed in human ovarian cancer lines and primary tumours. Moreover IKKε over expression renders cells resistant to cis-platin, whereas IKKε knockdown restores cis-platin sensitivity (Guo et al., *The American Journal of Pathology,* 2009, 175, 324-333). These observations suggest that IKKε inhibitors may show efficacy in the treatment of certain cancers.

IKKε knockout mice are protected from high-fat diet induced obesity, chronic inflammation in liver and fat, hepatic steatosis, and whole body insulin resistance. Such mice also show increased energy expenditure via enhanced expression of the uncoupling protein UCP 1 (Chiang et al., *Cell,* 2009, 138, 961-975). These observations suggest that IKKε inhibitors may have efficacy in the treatment of obesity and related disorders such as diabetes.

In the innate immune system TBK1 is activated in response to lipopolysaccharide (from bacterial cell wall) engagement with Toll-like receptor 4 (TLR4) or double-stranded RNA (from double stranded RNA viruses) engagement of TLR3. It is also activated in response to pro-inflammatory cytokines such as TNF and interleukin-1 (IL-1). Once activated TBK1 phosphorylates and activates IRF3, a transcription factor that triggers the production of interferon-beta and chemokines, such as interleukin-8 (IL-8) and RANTES. These substances play a key role in mediating host defence against infection by bacteria and viruses. Mice that do not express IRF3 are resistant to LPS-induced septic shock. These observations suggest that an inhibitor of TBK1 may have efficacy for the treatment/prevention of septic shock and/or the treatment of inflammatory disease.

TBK-1 is also activated in response to hypoxia and stimulates the production of pro-angiogenic factors such as vascular endothelial growth factor (VEGF) and IL-1. The expression of TBK-1 rises 2.5-3 fold after 24 h of hypoxia, similar to the increase in expression of VEGF. The hypoxia-induced VEGF expression can be abolished by siRNA knockdown of TBK1. The level of TBK1 mRNA and protein is elevated in malignant colon and breast cancer cells. TBK1 is also recruited and activated by the RalB/Sec5 effector complex; in cancer cells, constitutive engagement of this pathway via chronic RalB activation, restricts the initiation of apoptotic programmes. The proto-oncogene KRAS is mutated in a wide array of human tumours most of which are aggressive and respond poorly to standard therapies. The knockdown of TBK1 in KRAS dependant tumour cell lines has been shown to cause cell death. These observations suggest that an inhibitor of TBK1 may have efficacy in the treatment of cancer (Barbie et al., *Nature,* 2009, 462, 5, 108-114). Both IKKε and TBK-1 have been shown to phosphorylate and activate Akt in a number of cancer cell lines (Ou et al., *Molecular Cell,* 2011, 41, 458-70; Xie et al., *PNAS,* 2011, 108, 16, 6474-6479). Akt is a major signalling kinase which acts as a hub in a number of pathways playing a pivotal role in cell proliferation and survival. Furthermore, shRNA knockdown of TBK-1 in a number of NSCLC cell lines has been shown to inhibit cell survival. These results were further validated by use of a small molecule dual inhibitor of TBK-1 and IKKε kinase which was able to inhibit both the phosphorylation of Akt and the proliferation of a TBK-1 knock-down sensitive NSCLC cancer cell line. This further indicates the potential for a TBK-1/IKKε inhibitor in the treatment of cancer (Ou et al., *Molecular Cell,* 2011, 41, 458-70).

In summary, for these and related reasons, aberrant IKKε and/or TBK1 activity can lead to various disease states. Disease states mediated by IKKε and/or TBK1 mechanisms include inflammatory and tissue repair disorders, particularly rheumatoid arthritis, inflammatory bowel disease, asthma and chronic obstructive pulmonary disorder (COPD); osteoarthritis, osteoporosis and fibrotic diseases; dermatosis including psoriasis, atopic dermatitis and ultraviolet radiation (UV)-induced skin damage; autoimmune diseases including systemic lupus erythematosus, multiple sclerosis, psoriatic arthritis, and alkylosing spondylitis; tissue and organ rejection, Alzheimer's disease, stroke, atherosclerosis, restenosis, obesity, diabetes, glomerulonephritis, cancer, including Hodgkin's disease, cachexia, inflammation associated with infection including certain viral infections, including acquired immune deficiency syndrome (AIDS), adult respiratory distress syndrome, Ataxia Telangiestasia, primary open angle glaucoma and septic shock.

Certain pyrimidinyl-amines are known to act as protein kinase inhibitors. For example, WO 2005/012262 and WO 2009/032861 disclose certain such compounds. In the former document, the compounds are stated to be inhibitors of one or more of CDK1, CDK2, CDK4, CDK7, CDK9, GSK3, aurora kinase, and PLK1. In the latter document, the compounds are stated to be inhibitors of protein kinases, e.g. c-Jun N-terminal kinases (JNK). Surprisingly, we have now found that certain pyrimidinyl-amines having a specific substitution pattern are selective inhibitors of IKKε and/or TBK1, which is unexpected in light of the teaching of WO 2005/012262 and WO 2009/032861. They are therefore expected to find utility in patient populations where aberrant IKKε and/or TBK1 activity leads to disease.

Accordingly, the present invention provides a compound of the general formula I:

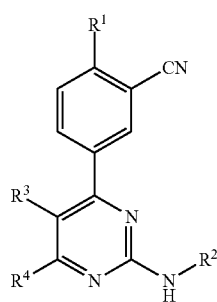

in which:
- $R^1$ represents an aliphatic heterocyclyl group having 4, 5, 6 or 7 ring atoms, bonded to the phenyl group shown in formula I through a ring nitrogen atom, and optionally substituted by one or more substituents selected from halogen; OH; =O; $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms and $NR^aR^b$ groups; $NO_2$; CN; $NR^aR^b$; $COR^c$; $O.CO.R^c$; $CO_2R^a$; $NR^a.COR^c$; $NR^aCO_2R^b$; $C(=NH)NH_2$; $SO_2R^c$; $NR^aSO_2R^c$; and $CH(CF_3)NH_2$;
- $R^2$ represents a phenyl or heteroaryl group which is optionally substituted by one or more substituents independently selected from:
  halogen atoms;
  $NR^aR^b$;
  $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms and $NR^aR^b$ groups; and
  —$(CH_2)_p$—R' in which p is 0, 1, 2, 3 or 4 and R' represents one of the following substituents: OH; $NO_2$; CN; $COR^c$; $O.CO.R^c$; $CO_2R^b$; $NR^a.COR^c$; $NR^aCO_2R^b$; $C(=NH)NH_2$; $SO_2R^c$; $NR^aSO_2R^c$; and $CH(CF_3)NH_2$;
  and/or which is optionally substituted on adjacent ring atoms by a group —$NR^a.CO.(CH_2)_n$— or —$(CH_2)_n.CO.NR^a$— forming a fused ring;
- $R^a$ represents a hydrogen atom or a $C_{1-4}$alkyl group;
- $R^b$ represents a hydrogen atom, a $C_{1-4}$alkyl group optionally substituted by a group $NR^aR^a$, or a cycloalkyl group in which a $CH_2$ moiety may be replaced by an oxygen atom or an $NR^a$ group;
- $R^c$ represents a hydrogen atom, a group —$NR^aR^b$, or a $C_{1-4}$alkyl group optionally substituted by a group $NR^aR^b$;
- or $R^a$ and $R^b$ together may, when attached to the same nitrogen atom, represent a —$(CH_2)_m$— group in which a $CH_2$ moiety may be replaced by an oxygen atom or an —$NR^a$— group;
- m represents 4 or 5;
- n represents 1 or 2; and
- each of $R^3$ and $R^4$ independently represents a hydrogen atom or a $C_{1-4}$alkyl group; or a salt thereof.

In one embodiment of the invention, $R^2$ represents a phenyl group optionally substituted by one or more of the substituents specified above. In another embodiment, $R^2$ represents a heteroaryl group optionally substituted by one or more of the substituents specified above. Except where the context requires otherwise, it should be understood that any preferences or specific embodiments mentioned in this Specification may apply to compounds in which $R^2$ is optionally substituted phenyl; similarly, any preferences mentioned in this Specification may apply to compounds in which $R^2$ is optionally substituted heteroaryl.

The compounds of the invention are inhibitors of the IKKε and/or TBK-1 receptors, and are therefore useful in the treatment of diseases associated with or caused by aberrant IKKε and/or TBK-1 activity.

An alkyl group may be either straight chain or branched. Examples of alkyl groups include methyl, ethyl, n-propyl, iso-propyl, n-butyl, t-butyl, i-butyl, and sec-butyl groups. Among unbranched alkyl groups, there are preferred methyl, ethyl, n-propyl, and n-butyl groups. Among branched alkyl groups, there may be mentioned iso-propyl, t-butyl, i-butyl, 1-ethylpropyl, 1-ethylbutyl, and 1-ethylpentyl groups.

An alkoxy group is the group O-alkyl, where "alkyl" is used as described above. Examples of alkoxy groups include methoxy and ethoxy groups. Other examples include propoxy and butoxy.

An alkenyl group may be straight chain or branched, and contains at least one carbon-carbon double bond. Examples of alkenyl groups include ethenyl, propenyl, and butenyl. Preferred alkenyl groups include ethenyl, 1-propenyl and 2-propenyl.

An alkynyl group may be straight chain or branched, and contains at least one carbon-carbon triple bond. Examples of alkynyl groups include ethynyl, propynyl, and butynyl. Preferred alkynyl groups include ethynyl, 1-propynyl and 2-propynyl.

A cycloalkyl group may be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, a cycloalkyl group is monocyclic, and preferably it has up to 7 carbon atoms.

Halogen means fluorine, chlorine, bromine or iodine. Fluorine, chlorine and bromine are particularly preferred.

A heterocyclyl group is a cyclic group of carbon atoms wherein from one to three of the carbon atoms is/are replaced by one or more heteroatoms independently selected from nitrogen, oxygen or sulfur. It may be aromatic or aliphatic. A heteroaryl group may, for example, be monocyclic or bicyclic. In a bicyclic heterocyclyl group there may be one or more heteroatoms in each ring, or only in one of the rings. A heteroatom is preferably O or N. Heterocyclyl groups containing a suitable nitrogen atom include the corresponding N-oxides and the corresponding S-mono- or di-oxides.

$R^1$ preferably has 4, 5 or 6, especially 5 or 6, atoms in the ring of which one or more may be a nitrogen, oxygen and/or sulphur atom in addition to the nitrogen atom through which the group is bonded to the phenyl group shown in formula I. For example, $R^1$ may represent a pyrrolidine, morpholine, piperazine, piperidine, azetidine, thiomorpholine or homopiperazine ring. When $R^1$ has 4 atoms in the ring, it may for example be an azetidine ring. Preferably $R^1$ represents a pyrrolidine ring. Any nitrogen atom in the ring in addition to the nitrogen atom through which the ring is bonded to the phenyl group in formula I, may carry an $R^b$ group, while any sulfur atom in the ring may be in any desired degree of oxidation, i.e. it may be —S—, —SO—, or —SO$_2$—.

$R^1$ may carry one or more, for example up to 3, especially one, optional substituent(s). If a $C_{1-4}$alkyl, $C_{1-4}$alkoxy, $C_{1-4}$alkoxy$C_{1-4}$alkyl, $C_{2-4}$alkenyl or $C_{2-4}$alkynyl substituent is present, this may for example be substituted by one or more, for example 1 to 3, halogen atoms, for example chlorine and/or fluorine atoms, and/or $NR^aR^b$ groups. Such a substituent may for example be a methyl, methoxy, trifluoromethyl, trifluoromethoxy, difluoromethyl or difluoromethoxy group. Preferred substituents for $R^1$ include halogen atoms, for example one or two fluorine atoms; OH; =O; methyl; methoxy; trifluoromethyl; trifluoromethoxy; CN; $NR^aR^b$; $COR^c$; $O.CO.R^c$; $CO_2R^a$; $NR^a.COR^c$; and $NR^aCO_2R^b$; in each of which each of $R^a$, $R^b$ and $R^c$ preferably independently represents an alkyl group, especially a methyl group, or a hydrogen atom, or $R^c$ may also represent an $NR^aR^b$ group, for example an $NH_2$ group. The presence of one or more polar substituents, for example hydroxy, =O, or $CO.NR^aR^b$, may be desired. For example, $R^1$ may be unsubstituted or substituted by one or two fluorine atoms, a hydroxy group (for example a 3-hydroxy group), an =O group, a methyl group, or a $CO.NH_2$ group. A hydroxy group is a preferred substituent. One or two fluorine atoms are also preferred substituents.

A heteroaryl group $R^2$ may for example be a heteroaromatic group having up to 10 ring atoms including up to 3, for example 1 or 2, hetero atoms. Preferably it has 5 or 6 ring atoms; for example it may be a pyridine, pyrazole, isoxazole, oxazole, imidazole, thioazole, 1,3,4-oxadiazole, 1,3,4-oxathiazole, pyrimidine or thiophene ring. $R^2$ may for example be a pyridine, pyrazole (for example a 2-methyl-2H-pyrazole-3-yl, hereinafter referred to as 2-Me-pyrazole), oxazole, isoxazole, thiazole or phenyl ring. Preferably $R^2$ represents a pyrazole (for example a 2-Me-pyrazole or 1-methyl-1H-pyrazol-4-yl (hereinafter referred to as 1-Me-pyrazole)) or, especially, a phenyl or pyridyl ring.

The group $R^2$ may be unsubstituted or substituted, for example by up to 3, for example 1, optional substituent(s). If a $C_{1-4}$alkyl, $C_{1-4}$alkoxy, $C_{1-4}$alkoxy $C_{1-4}$alkyl, $C_{2-4}$alkenyl or $C_{2-4}$alkynyl substituent is present, this may for example be substituted by one or more, for example 1 to 3, halogen atoms, for example chlorine and/or fluorine atoms, and/or $NR^aR^b$ groups. Such a substituent may for example be a methyl, methoxy, trifluoromethyl, trifluoromethoxy, difluoromethyl or difluoromethoxy group, or a group of formula $(CH_2)_xNR^aR^b$ or $O(CH_2)_xNR^aR^b$ in which x is 1, 2, 3 or 4, for example 1 or 2 or 3. In a group of formula $(CH_2)_xNR^aR^b$, x is preferably 1 or 2; in a group of formula $O(CH_2)_xNR^aR^b$, x is preferably 2 or 3. $R^a$ and $R^b$ may have one of the preferred meanings given below.

Preferred substituents for $R^2$ include halogen atoms; $NR^aR^b$; $C_{1-4}$alkyl optionally substituted by $NR^aR^b$; $C_{1-4}$alkoxy optionally substituted by $NR^aR^b$; —$CONR^aR^b$; $NR^aCOR^c$; or $SO_2R^c$. Examples of such substituents include the following, where R" represents a hydrogen atom or a $C_{1-4}$alkyl group, for example a methyl group: R"; OR"; CO.NR"R"; NR".CO.R"; NR".CO.CH$_2$NR"R"; SO$_2$R"; 4-morpholine; NR".CO.1-pyrrolidine; 1-(4-R"piperazine); NR"(CH$_2$)$_2$NR"R"; CO.NR"; CO-1-(4-R"piperazine); CO.NR".4-(1-R"piperidine); and CO.NR".(CH$_2$)$_2$.NR"R". Specific examples include: Me; OMe; CONH$_2$; NH.CO.Me; NH.CO.CH$_2$NMe$_2$; CO.NH$_2$; SO$_2$Me; 4-morpholine; NH.CO.1-pyrrolidine; 1-(4-Me-piperazine); NMe$_2$; NMe.CO.Me; NH.(CH$_2$)$_2$.NMe$_2$; NMe.(CH$_2$)$_2$.NMe$_2$; CO.1-(4-Me-piperazine); CO.NH.4-(1-Me-piperidine); and CO.NH.(CH$_2$)$_2$.NMe$_2$.

When $R^2$ represents a pyridyl or phenyl group, it is preferably substituted by at least one substituent selected from halogen, —$NR^aR^b$, $C_{1-4}$alkoxy, —$NR^a.CO.R^c$, —CO.N$R^aR^b$, and $SO_2C_{1-4}$alkyl (especially the specifically mentioned examples of such groups listed above) and also optionally substituted by one or more $C_{1-4}$alkyl, for example methyl, groups. Preferably such a group is a pyridyl or phenyl group substituted by one or more, preferably one, substituent selected from halogen, —$NR^aR^b$, —$C_{1-4}$alkoxy, —$NR^a.CO.R^c$, —$CO.NR^aR^b$, and $SO_2C_{1-4}$alkyl, especially $NR^a.CO.R^c$, —$CO.NR^aR^b$, and $SO_2C_{1-4}$alkyl; or selected from $C_{1-4}$alkoxy substituted by $NR^aR^b$, for example NMe$_2$, and $NR^aR^b$ in which $R^a$ and $R^b$ together represent an N-Me-piperidine-4-yl group.

When $R^2$ is a group other than a pyridyl or phenyl group, for example a pyrazole or an isoxazole ring, it is preferably either unsubstituted or substituted by one or more, preferably one, of the substituents mentioned above, for example a $C_{1-4}$alkyl group, for example a methyl group. For example, $R^2$ may be a 2-methyl-2H-pyrazol-3-yl or a 3-methyl-isoxazol-5-yl group.

In another preferred embodiment, $R^2$ is a group, for example a pyridyl or, especially, a phenyl group, which is substituted on adjacent ring atoms by a group —$NR^a.CO.(CH_2)_n$— or —$(CH_2)_n.CO.NR^a$— forming a fused ring. For example, $R^2$ may represent:

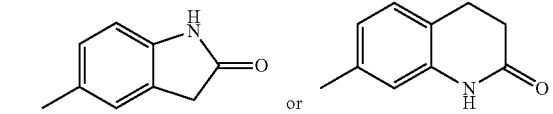

or

Compounds in which $R^2$ contains at least one substituent which includes a heteroatom, specifically O or N, deserve particular mention. Such substituents include $SO_2C_{1-4}$alkyl, $C_{1-4}$alkoxy and $C_{1-4}$alkoxy$C_{1-4}$alkyl groups, but are preferably groups which include an amine or amide moiety, e.g. $NR^aR^b$; $C_{1-4}$alkyl, $C_{1-4}$alkoxy, $C_{1-4}$alkoxy$C_{1-4}$alkyl, $C_{2-4}$alkenyl and $C_{2-4}$alkynyl groups, each substituted by one or more, preferably one, $NR^aR^b$ groups; and —$(CH_2)_p$—R' in which p is 0, 1, 2, 3 or 4 and R' represents $NR^a.COR^c$ or $NR^aCO_2R^b$, or R' represents $COR^c$ or $O.CO.R.^c$ in which $R^c$ represents $NR^aR^b$ or a $C_{1-4}$alkyl group substituted by a group $NR^aR^b$, or R' represents $CO_2R^b$, in which $R^b$ represents a $C_{1-4}$alkyl group substituted by $NR^aR^a$. Groups of the following formulae in which R" has the meaning given above, may for example be present: CO.NR"R"; NR".CO.R"; 4-morpholine; NR".CO.1-pyrrolidine; 1-(4-R"piperazine); NR"(CH$_2$)$_2$N R"R"; CO.NR"; CO-1-(4-R"piperazine); CO.NR".4-(1-R"piperidine); and CO.NR".(CH$_2$)$_2$.NR"R". Compounds in which $R^2$ is a group which is substituted on adjacent ring atoms by a group —$NR^a.CO.(CH_2)_n$— or —$(CH_2)_n.CO.NR^a$— forming a fused ring, may also be regarded as containing a substituent of this type.

Substituents as mentioned above, i.e. containing a heteroatom, may also advantageously be present in $R^1$.

Preferably each of $R^3$ and $R^4$ independently represents a methyl group or, preferably, a hydrogen atom. Preferably both of $R^3$ and $R^4$ are hydrogen atoms.

If the compound of the invention contains more than one moiety represented by $R^a$, these may be the same or different. Except whether otherwise stated, preferably $R^a$ is a methyl group or, especially, a hydrogen atom. If the compound of the invention contains more than one moiety represented by $R^b$, these may be the same or different. Where $R^b$ is a $C_{1-4}$alkyl group substituted by a group $NR^aR^a$, this may for example be a group $(CH_2)_xNR^aR^a$ where x is 1, 2, 3 or 4, for example 2, 3 or 4, especially 2 or 3. Where $R^b$ is a cycloalkyl group in which a $CH_2$ moiety may be replaced by an oxygen atom or an $NR^a$ group, it may for example have from 4 to 7, for example 5 or 6, ring atoms; it may for example be a piperidine, for example a 4-piperidine, group. $R^b$ may for example be a methyl group or, especially, a hydrogen atom. If $R^a$ and $R^b$ together represent a $—(CH_2)_m—$ group in which a $CH_2$ moiety may be replaced by an oxygen atom or an $—NR^a—$ group, it may for example be $—(CH_2)_4—$, $—(CH_2)_5—$, $—(CH_2)_2.O(CH_2)_2—$ or $—(CH_2)_2.NR^b.(CH_2)_2—$, in which $R^b$ is preferably a hydrogen atom or a methyl group.

Except where otherwise stated, preferably $R^c$ is a group $NR^aR^b$. For example, $R^c$ may be a group $NR^aR^b$ in which each of $R^a$ and $R^b$ represents a hydrogen atom or a methyl group.

Except whether otherwise stated, p is preferably 0, 1 or 2. For example, p may be 1; or p may be 0.

One preferred embodiment comprises compounds of the invention in which $R^1$ represents a pyrrolidine ring which may be substituted, for example by a hydroxy group or a $CO.NH_2$ group, or by one or more halogen, especially fluorine, atoms, or which is unsubstituted; $R^2$ represents a pyridine, pyrazole, oxazole, isoxazole, thioazole or phenyl ring, preferably pyrazole or, especially, phenyl or pyridyl, which is optionally substituted, preferably mono-substituted, by one or more substituents selected from $—NR^aR^b$, $C_{1-4}$alkoxy, $—NR^a.CO.R^c$, $—CO.NR^aR^b$, and $SO_2C_{1-4}$alkyl; or in which $R^2$ represents a pyridine, pyrazole, oxazole, isoxazole, thioazole or phenyl ring, preferably pyrazole (especially 2-Me-pyrazole) or, especially, phenyl or pyridyl, which is substituted on adjacent ring atoms by a group $—NR^a.CO.(CH_2)_n—$ or $—(CH_2)_n.CO.NR^a—$ forming a fused ring; and each of $R^3$ and $R^4$ represents a hydrogen atom.

Thus, especially preferred compounds of the invention include those in which $R^1$ represents an unsubstituted pyrrolidine ring; $R^2$ represents a 2-Me-pyrazole, phenyl or pyridyl ring which is mono-substituted by a substituent selected from $—NR^aR^b$, $C_{1-4}$alkoxy, $—NR^a.CO.R^c$, $—CO.NR^aR^b$, and $SO_2C_{1-4}$alkyl; or in which $R^2$ represents a phenyl or pyridyl ring, which is substituted on adjacent ring atoms by a group $—NR^a.CO.(CH_2)_n—$ or $—(CH_2)_n.CO.NR^a—$ forming a fused ring; and each of $R^3$ and $R^4$ represents a hydrogen atom. $R^a$, $R^b$ and $R^c$ suitably have one of the preferred meanings given above.

A further preferred embodiment comprises compounds of the invention in which $R^1$ represents a morpholine, piperazine, piperidine, azetidine, thiomorpholine or homopiperazine ring, preferably a morpholine or piperazine ring, which may be substituted, for example by a hydroxy group or a $CO.NH_2$ group or a $NH_2$ or $NMe_2$ group, or which is unsubstituted; $R^2$ represents a pyridine, pyrazole, oxazole, isoxazole, thioazole or phenyl ring, preferably pyrazole (especially 1- or 2-Me-pyrazole) or, especially, phenyl or pyridyl, which is optionally substituted, preferably monosubstituted, by one or more substituents selected from $—NR^aR^b$, $C_{1-4}$alkoxy, $—NR^a.CO.R^c$, $—CO.NR^aR^b$, and $SO_2C_{1-4}$alkyl; or in which $R^2$ represents a pyridine, pyrazole, oxazole, isoxazole, thioazole or phenyl ring, preferably pyrazole or, especially, phenyl or pyridyl, which is substituted on adjacent ring atoms by a group $—NR^a.CO.(CH_2)_n—$ or $—(CH_2)_n.CO.NR^a—$ forming a fused ring; and each of $R^3$ and $R^4$ represents a hydrogen atom.

Thus, for example, compounds of the invention may include those in which $R^1$ represents a morpholine, piperazine, piperidine, azetidine, thiomorpholine or homopiperazine ring, preferably a morpholine or piperazine ring, which may be substituted, for example by a hydroxy group or a $CO.NH_2$ group or a $NH_2$ or $NMe_2$ group, or which is unsubstituted; $R^2$ represents a 2-Me-pyrazole, phenyl, or pyridyl ring which is mono-substituted by a substituent selected from $—NR^aR^b$, $C_{1-4}$alkoxy, $—NR^a.CO.R^c$, $—CO.NR^aR^b$, and $SO_2C_{1-4}$alkyl; or in which $R^2$ represents a phenyl or pyridyl ring, which is substituted on adjacent ring atoms by a group $—NR^a.CO.(CH_2)_n—$ or $—(CH_2)_n.CO.NR^a—$ forming a fused ring; and each of $R^3$ and $R^4$ represents a hydrogen atom. $R^a$, $R^b$ and $R^c$ suitably have one of the preferred meanings given above.

Preferred compounds of the invention include the following compounds, and their salts, especially their pharmaceutically acceptable salts:

5-(2-Phenylamino-pyrimidin-4-yl)-2-pyrrolidin-1-yl-benzonitrile
5-[2-(Pyridin-4-ylamino)-pyrimidin-4-yl]-2-pyrrolidin-1-yl-benzonitrile
5-[2-(Pyridin-2-ylamino)-pyrimidin-4-yl]-2-pyrrolidin-1-yl-benzonitrile
2-Pyrrolidin-1-yl-5-[2-(3-trifluoromethyl-phenylamino)-pyrimidin-4-yl]-benzonitrile
2-[4-(3-Cyano-4-pyrrolidin-1-yl-phenyl)-pyrimidin-2-ylamino]-oxazole-5-carboxylic acid amide
5-[2-(5-Methyl-isoxazol-3-ylamino)-pyrimidin-4-yl]-2-pyrrolidin-1-yl-benzonitrile
2-[4-(3-Cyano-4-pyrrolidin-1-yl-phenyl)-pyrimidin-2-ylamino]-oxazole-4-carboxylic acid amide
5-[4-(3-Cyano-4-pyrrolidin-1-yl-phenyl)-pyrimidin-2-ylamino]-2-methyl-2H-pyrazole-3-carboxylic acid amide
5-[2-(5-Methyl-thiazol-2-ylamino)-pyrimidin-4-yl]-2-pyrrolidin-1-yl-benzonitrile
5-[2-(Oxazol-2-ylamino)-pyrimidin-4-yl]-2-pyrrolidin-1-yl-benzonitrile
5-[2-(4-Methyl-thiazol-2-ylamino)-pyrimidin-4-yl]-2-pyrrolidin-1-yl-benzonitrile
4-[4-(3-Cyano-4-pyrrolidin-1-yl-phenyl)-pyrimidin-2-ylamino]-3-methyl-benzamide.
(R)-1-{4-[2-(6-Acetylamino-pyridin-3-ylamino)-pyrimidin-4-yl]-2-cyano-phenyl}-pyrrolidine-2-carboxylic acid methylamide Further preferred compounds of the invention include the following compounds, and their salts, especially their pharmaceutically acceptable salts:

5-[2-(3-Fluoro-phenylamino)-pyrimidin-4-yl]-2-pyrrolidin-1-yl-benzonitrile
5-[2-(4-Fluoro-phenylamino)-pyrimidin-4-yl]-2-pyrrolidin-1-yl-benzonitrile
5-[2-(3-Methoxy-phenylamino)-pyrimidin-4-yl]-2-pyrrolidin-1-yl-benzonitrile
5-[2-(Pyridin-3-ylamino)-pyrimidin-4-yl]-2-pyrrolidin-1-yl-benzonitrile
5-[2-(3-Methyl-isoxazol-5-ylamino)-pyrimidin-4-yl]-2-pyrrolidin-1-yl-benzonitrile
5-[2-(2-Methyl-2H-pyrazol-3-ylamino)-pyrimidin-4-yl]-2-pyrrolidin-1-yl-benzonitrile
5-[2-(1-Methyl-1H-pyrazol-3-ylamino)-pyrimidin-4-yl]-2-pyrrolidin-1-yl-benzonitrile
N-{5-[4-(3-Cyano-4-morpholin-4-yl-phenyl)-pyrimidin-2-ylamino]-pyridin-2-yl}-acetamide
N-(5-{4-[3-Cyano-4-(4-methyl-piperazin-1-yl)-phenyl]-pyrimidin-2-ylamino}-pyridin-2-yl)-acetamide 5-[4-(3-Cyano-4-pyrrolidin-1-yl-phenyl)-pyrimidin-2-ylamino]-1-methyl-1H-pyrazole-3-carboxylic acid amide
1-{4-[2-(6-Acetylamino-pyridin-3-ylamino)-pyrimidin-4-yl]-2-cyano-phenyl}-piperidine-4-carboxylic acid amide
(R)-1-{4-[2-(6-Acetylamino-pyridin-3-ylamino)-pyrimidin-4-yl]-2-cyano-phenyl}-pyrrolidine-2-carboxylic acid amide
2-((S)-3-Hydroxy-pyrrolidin-1-yl)-5-[2-(2-methyl-2H-pyrazol-3-ylamino)-pyrimidin-4-yl]-benzonitrile
(R)-1-{2-Cyano-4-[2-(2-methyl-2H-pyrazol-3-ylamino)-pyrimidin-4-yl]-phenyl}-pyrrolidine-2-carboxylic acid amide.
5-[2-(1-Methyl-1H-imidazol-4-ylamino)-pyrimidin-4-yl]-2-pyrrolidin-1-yl-benzonitrile
5-{2-[6-(2-Dimethylamino-ethylamino)-pyridin-3-ylamino]-pyrimidin-4-yl}-2-(4-hydroxy-piperidin-1-yl)-benzonitrile
1-{4-[2-(6-Acetylamino-pyridin-3-ylamino)-pyrimidin-4-yl]-2-cyano-phenyl}-piperidine-4-carboxylic acid methylamide
(S)-1-{4-[2-(6-Acetylamino-pyridin-3-ylamino)-pyrimidin-4-yl]-2-cyano-phenyl}-pyrrolidine-2-carboxylic acid amide
(R)-1-(2-Cyano-4-{2-[6-(2-dimethylamino-ethylamino)-pyridin-3-ylamino]-pyrimidin-4-yl}-phenyl)-pyrrolidine-2-carboxylic acid amide
2-{3-[4-(3-Cyano-4-pyrrolidin-1-yl-phenyl)-pyrimidin-2-ylamino]-pyrazol-1-yl}-acetamide
5-[2-(3-Methyl-3H-imidazol-4-ylamino)-pyrimidin-4-yl]-2-pyrrolidin-1-yl-benzonitrile Especially preferred compounds of the invention include the following compounds, and their salts, especially their pharmaceutically acceptable salts:

5-[2-(4-Methoxy-phenylamino)-pyrimidin-4-yl]-2-pyrrolidin-1-yl-benzonitrile
3-[4-(3-Cyano-4-pyrrolidin-1-yl-phenyl)-pyrimidin-2-ylamino]-benzamide
N-{3-[4-(3-Cyano-4-pyrrolidin-1-yl-phenyl)-pyrimidin-2-ylamino]-phenyl}-acetamide
4-[4-(3-Cyano-4-pyrrolidin-1-yl-phenyl)-pyrimidin-2-ylamino]-benzamide
N-{4-[4-(3-Cyano-4-pyrrolidin-1-yl-phenyl)-pyrimidin-2-ylamino]-phenyl}-acetamide
5-[2-(3-Methanesulfonyl-phenylamino)-pyrimidin-4-yl]-2-pyrrolidin-1-yl-benzonitrile
5-[2-(2-Oxo-2,3-dihydro-1H-indol-5-ylamino)-pyrimidin-4-yl]-2-pyrrolidin-1-yl-benzonitrile
N-{5-[4-(3-Cyano-4-pyrrolidin-1-yl-phenyl)-pyrimidin-2-ylamino]-pyridin-2-yl}-acetamide
5-[2-(6-Morpholin-4-yl-pyridin-3-ylamino)-pyrimidin-4-yl]-2-pyrrolidin-1-yl-benzonitrile
5-[2-(2-Oxo-1,2,3,4-tetrahydro-quinolin-7-ylamino)-pyrimidin-4-yl]-2-pyrrolidin-1-yl-benzonitrile
Pyrrolidine-1-carboxylic acid {3-[4-(3-cyano-4-pyrrolidin-1-yl-phenyl)-pyrimidin-2-ylamino]-phenyl}-amide
5-{2-[6-(4-Methyl-piperazin-1-yl)-pyridin-3-ylamino]-pyrimidin-4-yl}-2-pyrrolidin-1-yl-benzonitrile
5-[2-(6-Dimethylamino-pyridin-3-ylamino)-pyrimidin-4-yl]-2-pyrrolidin-1-yl-benzonitrile
N-{4-[4-(3-Cyano-4-pyrrolidin-1-yl-phenyl)-pyrimidin-2-ylamino]-phenyl}-N-methyl-acetamide
N-(5-{4-[3-Cyano-4-((S)-3-hydroxy-pyrrolidin-1-yl)-phenyl]-pyrimidin-2-ylamino}-pyridin-2-yl)-acetamide
5-{2-[6-(2-Dimethylamino-ethylamino)-pyridin-3-ylamino]-pyrimidin-4-yl}-2-pyrrolidin-1-yl-benzonitrile
5-(2-{6-[(2-Dimethylamino-ethyl)-methyl-amino]-pyridin-3-ylamino}-pyrimidin-4-yl)-2-pyrrolidin-1-yl-benzonitrile
5-{2-[3-(4-Methyl-piperazine-1-carbonyl)-phenylamino]-pyrimidin-4-yl}-2-pyrrolidin-1-yl-benzonitrile
3-[4-(3-Cyano-4-pyrrolidin-1-yl-phenyl)-pyrimidin-2-ylamino]-N-(1-methyl-piperidin-4-yl)-benzamide
3-[4-(3-Cyano-4-pyrrolidin-1-yl-phenyl)-pyrimidin-2-ylamino]-N-(2-dimethylamino-ethyl)-benzamide
N-{5-[4-(3-Cyano-4-pyrrolidin-1-yl-phenyl)-pyrimidin-2-ylamino]pyridin-2-yl}-2-dimethylamino-acetamide
2-((S)-3-Hydroxy-pyrrolidin-1-yl)-5-{2-[6-(4-methyl-piperazin-1-yl)-pyridin-3-ylamino]pyrimidin-4-yl}-benzonitrile
(R)-1-(2-Cyano-4-{2-[6-(4-methyl-piperazin-1-yl)-pyridin-3-ylamino]-pyrimidin-4-yl}-phenyl)-pyrrolidine-2-carboxylic acid amide.
3-[4-(3-Cyano-4-pyrrolidin-1-yl-phenyl)-pyrimidin-2-ylamino]-benzoic acid
5-[2-(1-Methyl-1H-pyrazol-4-ylamino)-pyrimidin-4-yl]-2-pyrrolidin-1-yl-benzonitrile
5-{2-[6-(2-Dimethylamino-ethoxy)-pyridin-3-ylamino]-pyrimidin-4-yl}-2-pyrrolidin-1-yl-benzonitrile
5-[2-(6-Methoxy-pyridin-3-ylamino)-pyrimidin-4-yl]-2-pyrrolidin-1-yl-benzonitrile
5-{2-[6-(2-Dimethylamino-ethylamino)-pyridin-3-ylamino]-pyrimidin-4-yl}-2-((S)-3-hydroxy-pyrrolidin-1-yl)-benzonitrile
5-{2-[6-(2-Dimethylamino-ethylamino)-pyridin-3-ylamino]-pyrimidin-4-yl}-2-((S)-2-methyl-pyrrolidin-1-yl)-benzonitrile
1-(2-Cyano-4-{2-[6-(2-dimethylamino-ethylamino)-pyridin-3-ylamino]-pyrimidin-4-yl}-phenyl)-piperidine-4-carboxylic acid amide
N-(5-{4-[3-Cyano-4-(3-hydroxy-azetidin-1-yl)-phenyl]-pyrimidin-2-ylamino}-pyridin-2-yl)-acetamide
5-{2-[6-(2-Dimethylamino-ethylamino)-pyridin-3-ylamino]-pyrimidin-4-yl}-2-((S)-3-fluoro-pyrrolidin-1-yl)-benzonitrile
N-(5-{4-[3-Cyano-4-((R)-2-methoxymethyl-pyrrolidin-1-yl)-phenyl]-pyrimidin-2-ylamino}-pyridin-2-yl)-acetamide
N-(5-{4-[3-Cyano-4-((R)-3-hydroxy-pyrrolidin-1-yl)-phenyl]-pyrimidin-2-ylamino}-pyridin-2-yl)-acetamide
2-((S)-3-Hydroxy-pyrrolidin-1-yl)-5-[2-(1-methyl-1H-pyrazol-4-ylamino)-pyrimidin-4-yl]-benzonitrile
1-{2-Cyano-4-[2-(1-methyl-1H-pyrazol-4-ylamino)-pyrimidin-4-yl]-phenyl}-piperidine-4-carboxylic acid amide
N-(5-{4-[3-Cyano-4-((S)-3-methoxy-pyrrolidin-1-yl)-phenyl]-pyrimidin-2-ylamino}-pyridin-2-yl)-acetamide
2-((R)-3-Fluoro-pyrrolidin-1-yl)-5-{2-[6-(1-methyl-piperidin-4-ylamino)-pyridin-3-ylamino]-pyrimidin-4-yl}-benzonitrile
2-((S)-3-Fluoro-pyrrolidin-1-yl)-5-{2-[6-(1-methyl-piperidin-4-ylamino)-pyridin-3-ylamino]-pyrimidin-4-yl}-benzonitrile
2-((S)-3-Hydroxy-pyrrolidin-1-yl)-5-{2-[6-(1-methyl-piperidin-4-ylamino)-pyridin-3-ylamino]-pyrimidin-4-yl}-benzonitrile
2-(3,3-Difluoro-pyrrolidin-1-yl)-5-{2-[6-(1-methyl-piperidin-4-ylamino)-pyridin-3-ylamino]-pyrimidin-4-yl}-benzonitrile The invention includes salts of compounds of the general formula I. Generally, the compounds form addition salts with acids such as, for example, mineral acids, strong organic carboxylic acids, such as alkanecarboxylic acids, for example of 1 to 4 carbon atoms, which are unsubstituted or substituted, for example, by halogen, such as saturated or unsaturated dicar-boxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts generally include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluene-sulfonic, formic, benzoic, malonic, naphthalene-2-sulfonic, benzenesulfonic, isethionic, ascorbic, malic, phthalic, aspartic, and glutamic acids, lysine and arginine. Salts which are not themselves pharmaceutically acceptable, for example those derived from acids such as oxalic, may be useful as intermediates in obtaining the compounds of the invention and their pharmaceutical acceptable acid addition salts.

Depending upon the substituents present, the compounds of formula I may also form salts with bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

The compounds of the invention may also form solvates, for example hydrates, and these are also included within the scope of the present invention.

Depending upon the substituents present in the compounds of the general formula I, the compounds may exist as stereoisomers and/or geometric isomers. All individual stereoisomers and geometric isomers, as well as mixtures thereof, are included within the scope of the invention. Further, isotopic forms, for example where a hydrogen atom is replaced with deuterium, are included within the invention. Certain isotopic forms may have beneficial biological properties, for example improved metabolic stability or enhanced therapeutic activity over other isotopic forms; or a specific isotopic form may be useful for biological imaging purposes, for example carbon-11, nitrogen-13, oxygen-15 or fluorine 18 isotopic variants may be used for positron emission tomography.

The invention also provides a process for the preparation of a compound of the invention, which comprises either:

(a) reacting a compound of the general formula II:

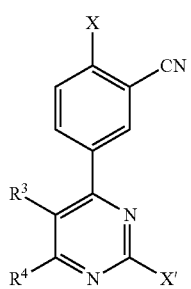

II with amines of the general formula $R^2NH_2$ and $R^1H$; or (b) reacting a compound of formula III

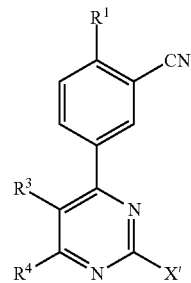

III with a compound of the general formula $R^2NH_2$; or (c) reacting a compound of formula IV

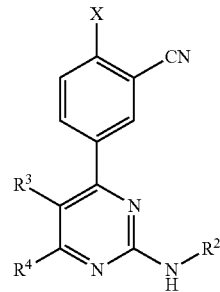

IV with a compound of the general formula $R^1H$; in which X represents a leaving group, X' represents a leaving group, and $R^1$ and $R^2$ have the meanings given for the general formula I.

Depending upon the meanings of $R^1$ and $R^2$, certain of the intermediates II-IV are novel, and the invention also provides these intermediates per se.

The leaving group X and X' in compounds of the general formula II, III and IV may for example be a halogen atom or an alkyl (preferably methyl)sulfone or sulfoxide group. Nucleophilic SnAr displacement chemistry can be used to insert the $R^1$ or $NR^2$ groups in which case X or X' is preferably fluorine, chlorine, or an alkyl (preferably methyl)sulfone or sulfoxide group.

Alternatively palladium catalysed Buchwald-Hartwig type chemistry can be used in which case X or X' is preferably chlorine, bromine or iodine. The use of different X and X' groups in conjunction with either SnAr or palladium catalysed chemistry can be used to control the differential reactivity at either centre. For example if X is fluorine and X' is chlorine then palladium catalysed coupling can be used between a compound of formula II and an amine of formula $R^2NH_2$ to give a compound of formula IV.

SnAr reactions are generally carried out in the presence of the amine, with heating if required, for example between 100-180° C. The reaction may for example be carried out using conventional heating at ambient pressure under reflux conditions, or in a sealed tube, alternatively a microwave reactor can be employed. A suitable solvent, for example NMP, nBuOH or DMF, may be used if desired.

The addition of a suitable base for example DIPEA or $K_2CO_3$ may help catalyse the reaction. Alternatively the addition of for example 0.5-2 equivalents of HCl can also be used to catalyse the reaction when an aryl or heteroaryl amine is used as the reaction partner.

Buchwald-Hartwig type reactions generally involve reacting the 2-chloro, 2-bromo or 2-iodo-compound with the requisite amine in the presence of a palladium catalyst. Examples of conditions that can be used to carry out such transformations are described in WO 2008/62044.

Compounds of the general formula III may be made by methods analogous to known methods. One such method is via a Suzuki-Miyaura cross coupling of a boronic acid or boronic ester of the general formula V:

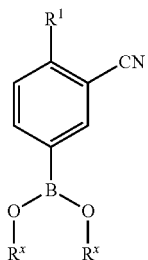

in which each $R^x$ may be H or alkyl, or the two $R^x$ groups may be linked so as to form a cyclic boronic ester; with a pyrimidine of the general formula VI:

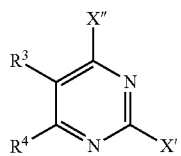

in which X' has the meaning given in formula II and III and X" is chlorine, bromine or iodine, preferably X' and X" are the same or if different X' is fluorine, chlorine or an alkyl (preferably methyl)sulfone or sulfoxide group. Typical boronic esters used include for example the dimethylboronic ester and the pinacol ester. The compound of formula VI may for example be 2,4-diiodopyrimidine or 2,4-dichloropyrimidine. 2,4-Diiodo-pyrimidine may be prepared from 2,4-dichloro-pyrimidine by reaction with aqueous hydroiodic acid.

Compounds of the general formula V may be prepared for example through the displacement of the corresponding halide of the general formula VII:

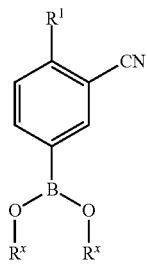

in which X is preferably fluoride or chloride, with a compound of the formula $R^1H$. Heating, for example between 100-180° C., may be applied if desired. Compounds of formula VII can be purchased from commercial suppliers and methods for their synthesis are known in the art.

Compounds of formula II may be prepared from compounds of formula VII and compounds of formula VI using methods analogous to those described above for the synthesis of compounds of formula III.

Aberrant kinase activity has been implicated in many diseases. For example, JNK has been implicated in diseases which involve excitotoxicity of hippocampal neurons, for example stroke, spinal cord injury, multiple sclerosis and head trauma; ischemiareperfusion injury and conditions which may lead to or otherwise be associated with this, for example stroke, myocardial infarction, congestive heart failure, cardiac hypertrophy and atherosclerosis. JNK has also been associated with neurodegenerative diseases such as Parkinsons and Alzheimers diseases; neural tube birth defect; chronic inflammatory diseases such as rheumatoid arthritis and atherosclerosis; obesity and insulin resistant diabetes; and cancer. It is known that for many diseases wherein individual patients display the same gross symptomology, for example breast cancer, the disease may be caused and sustained by a number of different biochemical mechanisms which will vary from patient to patient. For many such diseases, the effectiveness of any treatment will therefore be highly dependent upon the biochemical mechanisms that precipitate and maintain the diseased state.

The compounds of the invention are inhibitors of IKKε and/or TBK-1, and are therefore useful in the treatment of diseases associated with, or caused by, aberrant IKKε and/or TBK-1 activity. Such diseases include inflammatory and tissue repair disorders, particularly rheumatoid arthritis, inflammatory bowel disease, asthma and chronic obstructive pulmonary disorder (COPD); osteoarthritis, osteoporosis and fibrotic diseases; dermatosis including psoriasis, atopic dermatitis and ultraviolet radiation (UV)-induced skin damage; autoimmune diseases including systemic lupus erythematosus, multiple sclerosis, psoriatic arthritis, and alkylosing spondylitis; tissue and organ rejection, Alzheimer's disease, stroke, atherosclerosis, restenosis, obesity, diabetes, glomerulonephritis, cancer, including Hodgkin's disease, cachexia, inflammation associated with infection including certain viral infections, including acquired immune deficiency syndrome (AIDS), adult respiratory distress syndrome, Ataxia Telangiestasia, primary open angle glaucoma and septic shock.

Because of the selectivity of the compounds of the invention to IKKε and TBK-1, rather than to other kinases such as JNK, it is expected that they may be used for treatment of disease with fewer side-effects than less selective compounds. It is also expected that they will find particular utility in targeting diseases in particular patient populations, i.e. where the disease is specifically caused by aberrant IKKε and/or TBK-1 activity.

In particular, the compounds of the invention are expected to be useful in the treatment of cancer, specifically, in the treatment of patient populations in which the disease is associated with aberrant IKKε and/or TBK-1 activity. IKKε has been implicated in breast cancer, including tamoxifen resistant breast cancer, ovarian cancer, including cis-platin resistant ovarian cancer, cancer in which tumour growth and/or survival is dependent upon IKKε kinase activity, cancers harbouring Ras mutations and Ras-dependant tumours, and cancers involving amplification of the 1q32 gene locus. TBK-1 has been implicated in cancers which harbour K-ras mutation and K-ras dependent tumours, cancers which harbour Ras mutations and cancers which are Ras-dependent, breast cancer, lung cancer, particularly non small cell lung cancer (NSCLC), ovarian cancer, prostate cancer, myeloma and leukemia.

In addition to cancer, specifically IKKε and/or TBK-1 associated cancers, the compounds of the invention are expected to be particularly useful in the treatment and prevention of obesity (in which IKKε is implicated); and diseases in which hypoxia-induced angiogenesis is important (which includes some cancers), the treatment and prevention of septic shock, and primary open angle glaucoma (in all of which TBK-1 is implicated).

The invention therefore provides a pharmaceutical composition which comprises a compound according to the invention, together with a pharmaceutically suitable carrier. Such compositions may contain the compound of the invention as the sole active ingredient, or they may contain an additional active ingredient.

The invention further provides a method of treating or preventing a disease mediated by IKKε and/or TBK-1 mechanisms in a subject, which comprises administration of a compound or a composition according to the invention, to the subject; a compound or a composition according to the invention for use in therapy, particularly for use in the treatment or prevention of any of the diseases mentioned above; and a compound according to the invention for use in the manufacture of a medicament for use in the treatment of any of the diseases mentioned above. Preferably the compound or composition is administered to a mammal, especially a human.

Whilst a compound of the invention may be used as the sole active agent, it is also possible for the compound to be used in combination with one or more further active agents. Such further active agents may be further compounds according to the invention, or they may be different therapeutic agents, for example agents targeting one of the diseases mentioned above, particularly the same disease as that targeted by the compound of the invention. The compound of the invention may be co-formulated with the additional agent, or it may be formulated separately and administered consecutively, simultaneously or sequentially with the additional agent.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician or veterinarian can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The pharmaceutical formulations according to the invention include those suitable for oral, parenteral (including subcutaneous, intradermal, intramuscular, intravenous (bolus or infusion), and intraarticular), inhalation (including fine particle dusts or mists which may be generated by means of various types of metered doses pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or, more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

It should be understood that in addition to the ingredients particularly mentioned above, the formulations of this invention may include other agents conventional in the art having regard to the type of formulation in question, for example those suitable for oral administration may include flavouring agents.

The following Examples illustrate the invention.
Abbreviations Used
Boc Tert-butoxycarbonyl
(Boc)$_2$O Di-tert-butyl dicarbonate
Dave-Phos 2-Dicyclohexylphosphino-2'-(NN-dimethylamino)biphenyl
DCM Dichloromethane
DMF N,N-Dimethylformamide
DMSO Dimethyl sulfoxide
EtOH Ethanol
EtOAc Ethyl acetate
Eqv. Equivalents
HCl Hydrochloric acid
HPLC High-performance liquid chromatography
LC-MS Liquid chromatography-mass spectrometry
MeCN Acetonitrile
MeOH Methanol
Min. Minute
MgSO$_4$ Magnesium sulfate
NaO$^t$Bu Sodium tert-butoxide
Na$_2$SO$_4$ Sodium sulfate
NMM N-Methyl morpholine
NMP N-Methylpyrrolidinone
Pd$_2$(dba)$_3$ Tris(dibenzylideneacetone)dipalladium(0)
Pet ether Petroleum ether
rt Room temperature
S.M. Starting Material
THF Tetrahydrofuran
ww weight with respect to weight ratio
Xantphos 4,5-Bis(diphenylphosphino)-9,9-dimethylxanthene
Analytical Methods Used
MeOH-FA: Phenomenex Luna C18 (2) 3 µm, 50×4.6 mm; A=water+0.1% formic acid; B=MeOH; 45° C.; % B: 0 min 5%, 1 min 37.5%, 3 min 95%, 3.51 min 5%, 4.5 min 5%; 2.25 mL/min.
ANALpH2_MeOH_QC: Phenomenex Luna C18 (2) 5 µm, 150×4.6 mm; 35° C.; A=water+0.1% formic acid; B=MeOH; 35° C.; % B: 0 min 5%, 0.5 min 5%, 7.5 min 95%, 10 min 95%, 10.1 min 5%, 13 min 5%; 1.5 mL/min.
Method X: Xterra MS C18 2.5 µm, 4.6×50 mm; A=water+0.1% formic acid; B=MeCN+0.1% formic acid; 25° C.; % B: 0 min 10%, 4 min 90%, 7.5 min 90%, 7.6 min 10%; 1.0 mL/min.
Method Y: Acquity UPLC BEH C18 1.7 µm, 2.1×50 mm; A=water+0.025% TFA; B=MeCN+0.025% TFA; 25° C.; % B: 0 min 15%, 3 min 95%, 4 min 95%, 4.1 min 15%; 0.4 mL/min.
Method Z: Acquity UPLC BEH C18 1.7 µm, 2.1×100 mm; A=water+0.025% TFA; B=MeCN+0.025% TFA; 25° C.; % B: 0 min 30%, 4 min 80%, 6 min 80%, 6.1 min 30%; 0.3 mL/min.
Method B: Zodiacsil C18 5 µm, 4.6×50 mm; A=water+0.01M ammonium formate; B=MeOH; 25° C.; % B: 0 min 60%, 3 min 90%, 8 min 90%, 8.1 min 60%; 1.0 mL/min.
Method C: Xterra MS C18 2.5 µm, 4.6×50 mm; A=water+0.1% formic acid; B=MeCN+0.1% formic acid; 25° C.; % B: 0 min 20%, 4 min 50%, 6 min 90%, 8.5 min 90%, 8.6 min 20%; 1.0 mL/min.
Method D: Xterra MS C18 2.5 µm, 4.6×50 mm; A=water+0.1% formic acid; B=MeCN+0.1% formic acid; 25° C.; % B: 0 min 10%, 4 min 90%, 7.5 min 90%, 7.6 min 10%, 8; 1.0 mL/min.
Method E: Acquity UPLC BEH C18 1.7 µm, 2.1×100 mm; A=water+0.025% TFA; B=MeCN+0.025% TFA; 25° C.; % B: 0 min 10%, 4 min 80%, 5 min 80%, 5.1 min 10%; 0.3 mL/min.
Method F: Acquity UPLC BEH C18 1.7 µm, 2.1×100 mm; A=water+0.025% TFA; B=MeCN+0.025% TFA; 25° C.; % B: 0 min 20%, 3 min 80%, 4 min 80%, 4.1 min 20%; 0.4 mL/min.
Method G: Acquity UPLC BEH C18 1.7 µm, 2.1×50 mm; A=water+0.025% TFA; B=MeCN+0.025% TFA; 25° C.; % B: 0 min 20%, 2 min 80%, 4 min 80%, 4.1 min 20%; 0.4 mL/min.

Method H: Zodiacsil C18 5 µm, 4.6×50 mm; A=water+0.01M ammonium formate; B=MeOH; 25° C.; % B: 0 min 5%, 4 min 90%, 10 min 90%, 10.1 min 5%; 1.0 mL/min.

Method I: Xterra MS C18 1.8 µm, 4.6×50 mm; A=water+0.1% formic acid; B=MeCN+0.1% formic acid; 25° C.; % B: 0 min 20%, 4 min 90%, 6 min 90%, 6.1 min 20%; 1.0 mL/min.

Biological Testing

Compounds of the invention (synthesised as described below) were tested for activity against the IKKϵ and TBK-1 enzyme as follows:

Inhibitions studies were performed using a time-resolved fluorescence-based Lanthascreen™ assay. Phosphorylation of a fluorescein-labelled substrate peptide is measured using terbium-labeled phosphospecific antibodies. Terbium is excited at 340 nm and the FRET energy transfer to fluorescein is measured at 495 and 520 nm. The emission ratio between 520 and 495 is a measure of the level of phosphorylation of the substrate by the kinase.

Kinase inhibition assays (10 µL) were performed at 20° C. in 384-well plate format. Compound IC50 values were determined at the apparent Km for ATP (20 µM) based on a radiometric assay (Invitrogen) using 8 or 10 point curves in duplicate. The final reaction conditions contained 400 nM fluorescein-IkBα substrate (DRHDSGLDSMKDE), 20 µM ATP, 2 nM or 8 nM IKKϵ or TBK1 kinase respectively, and 3% DMSO in kinase assay buffer consisting of 50 mM HEPES (pH 7.5), 10 mM MgCl, 1 mM EGTA, 0.01% Brij-35.

Compound dilutions were prepared from 10 mM DMSO stocks by dilution into DMSO. Compound dilution series were further diluted in kinase assay buffer to give a 12% DMSO stock, the final concentration in the assay being 3% DMSO.

The kinase phosphorylation assay was initiated by the addition of the kinase and the reaction was allowed to proceed for 1 hr or 2.5 hr for IKKϵ and TBK-1 kinase respectively. Both conditions were within the linearity of the phosphorylation. The reaction was stopped by the addition of 10 mM EDTA, and phosphorylation was detected after a 1 hr incubation with 1.5 nM terbium-labelled antibody against phosphorylation at Serine 32 on the IkBα☐peptide, both in TR-FRET dilution buffer (Invitrogen).

The results of the testing are show under Chemical Synthesis below. In the data presented for IKKϵ, <9 µM means having an activity in the range from 300 nM≤9 µM; and <300 nM means having an activity in the range 30 nM≤300 nM; and for the data presented for TBK-1, <3 µM means having an activity in the range 300 nM≤3 µM, and <300 nM means having an activity in the range 30 nM≤300 nM.

The compounds of examples DMX-1,8,9,14 and 16 were tested for activity against TBK1, IKKβ, Jnk1 and Jnk3 in addition to IKK-ϵ and TBK-1. TBK-1, IKKβ, Jnk1 and Jnk3 were screened using radiolabelled P$^{33}$ ATP using the Kinase Hotspot Technology of Reaction Biology Corp. Screening against Jnk-1 and Jnk-3 was carried out at the Km for ATP. IKK-ϵ and TBK-1 screening was also carried out as described above at the Km for ATP for these enzymes. When compounds were screened against TBK-1 using the radiolabelled P$^{33}$ ATP assay all of the compounds in the table showed >95% inhibition at 300 nM. Screening against IKK-β was carried out at a single point using 1 µM of ATP, percentage inhibitions shown in brackets. In addition the compounds of examples DMX-56, 66 and 69 were tested for activity against TBK-1, IKKβ and Jnk1 in addition to TBK-1 and IKKϵ. TBK-1, IKKβ and Jnk1 were screened using radiolabelled P$^{33}$ ATP using the Kinase Hotspot Technology of Reaction Biology Corp. IKK-ϵ and TBK-1 screening was also carried out as described above at the Km for ATP for these enzymes. When compounds were screened against TBK-1 using the radiolabelled P$^{33}$ ATP assay all of the compounds showed >95% inhibition at 300 nM. Screening against IKK-β and JNk-1 was carried out at a single point using 10 µM of ATP, percentage inhibitions shown in brackets.

| Example | Concentration of compounds required for ~ 50% inhibition (nM) | | | | |
|---|---|---|---|---|---|
| | IKK-ϵ | TBK-1 | IKK-β | Jnk-1 | Jnk-3 |
| DMX-1 | 2 | 4 | 1000 (48) | 254 | >10000 |
| DMX-8 | 3 | 3 | 1000 (50) | 354 | >10000 |
| DMX-9 | 3 | 3 | 1000 (34) | 262 | 10000 (51) |
| DMX-14 | 3 | 2 | 1000 (45) | 201 | >10000 |
| DMX-16 | 2 | 1 | 1000 (43) | 222 | >10000 |
| DMX-56 | 8 | 3 | 1000 (56) | >1000 (21) | — |
| DMX-66 | 21 | 24 | 1000 (43) | 1000 (52) | — |
| DMX-69 | 4 | 4 | 1000 (54) | 1000 (43) | — |

CHEMICAL SYNTHESIS EXAMPLES

Example DMX-1

Synthesis of 3-[4-(3-cyano-4-pyrrolidin-1-yl-phenyl)-pyrimidin-2-ylamino]-benzamide 2-pyrrolidin-1-yl-5-(4,4,5,5-tetramethyl-[1,3,2]dioxaborolan-2-yl)-benzonitrile

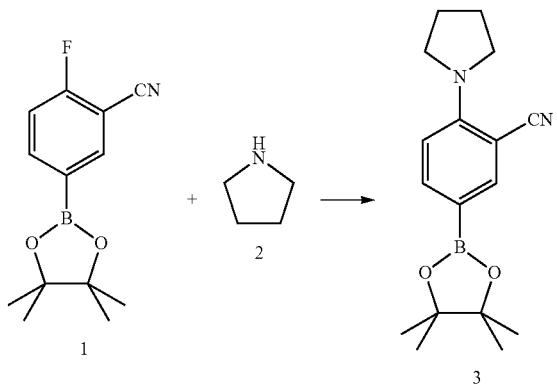 [SMILES: CC1(C)OB(c2ccc(F)c(C#N)c2)OC1(C)C ; C1CCNC1 ; CC1(C)OB(c2ccc(N3CCCC3)c(C#N)c2)OC1(C)C]

3-Cyano-4-fluorophenyl-boronic acid pinacol ester (250 mg, 1.01 mmol) was dissolved in NMP (4 mL). Pyrrolidine (415 µL, 5.05 mmol) was added and the mixture heated at 140° C. in the microwave (300 W, stirring) for 5 minutes. The reaction was repeated 14 more times. The 15 reaction mixtures were combined and the solvent evaporated in vacuo (Genevac™). The residue was dissolved in EtOAc (200 mL) and the solution washed with saturated brine solution (2×75 mL). The organic phase was dried (MgSO$_4$), filtered and the solvent evaporated in vacuo. The crude product was purified by flash column chromatography (40-63 mesh silica gel, 90% isohexane-EtOAc) to provide the title compound as an off-white solid (2.84 g, 63%); LC-MS, R$_t$=3.33 min (MeOH-FA method), m/z 298 (MH$^+$).

In addition to this procedure similar reactions may alternatively be accomplished by heating in DMF at 120° C. in a sealed tube or alternatively by heating in MeCN at 80° C.

5-(2-chloro-pyrimidin-4-yl)-2-pyrrolidin-1-yl-benzonitrile

In addition to this procedure similar reactions may alternatively be accomplished by heating in 1:1 1,4-dioxane-H₂O at 100-110° C. in a sealed tube.

3-[4-(3-cyano-4-pyrrolidin-1-yl-phenyl)-pyrimidin-2-ylamino]-benzamide (DMX-1)

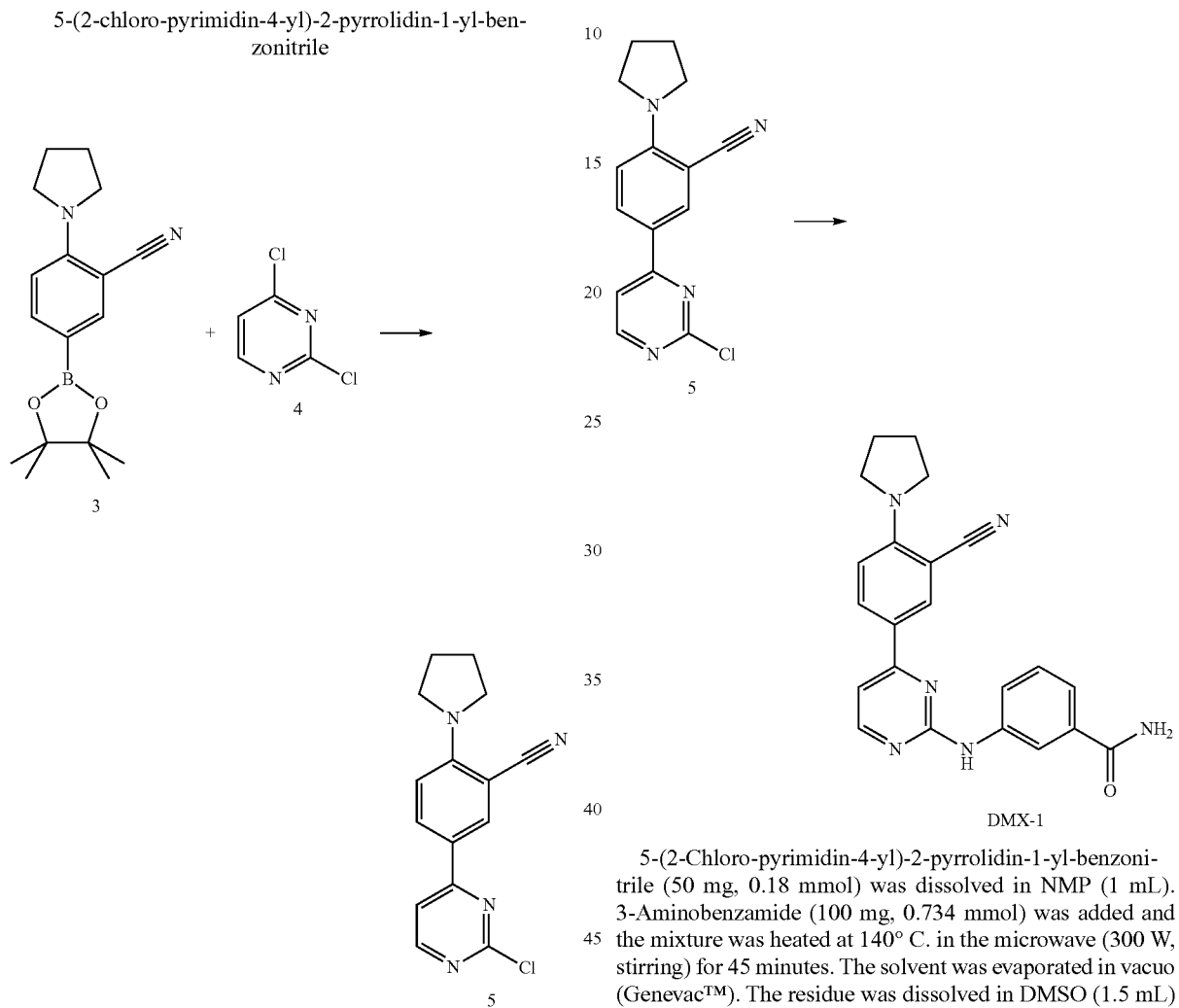

Pyrrolidin-1-yl-5-(4,4,5,5-tetramethyl-[1,3,2]dioxaborolan-2-yl)-benzonitrile (200 mg, 0.67 mmol), 2,4-dichloropyrimidine (120 mg, 0.81 mmol), tetrakis(triphenylphosphine) palladium(0) (78 mg, 0.07 mmol, 10 mol %) and sodium carbonate (213 mg, 2.01 mmol) were diluted with 1:1 1,4-dioxane-H₂O (4.0 mL). The mixture was then heated at 100° C. in the microwave (300 W, stirring) for 10 minutes. The reaction was repeated four more times. The reaction mixtures were combined and the solvents evaporated in vacuo (Genevac™). The residue was partitioned between DCM (150 mL) and H₂O (50 mL). The organic phase was washed with water (50 mL) and saturated brine solution (75 mL). The organic phase was then dried (MgSO₄), filtered and the solvent evaporated in vacuo. The crude product was purified by column chromatography (40-63 mesh silica gel, 70% isohexane-EtOAc) to provide the title compound as a yellow solid (727 mg, 76%); LC-MS, $R_t$=2.80 min (MeOH-FA method), m/z 285, 287 (MH⁺).

5-(2-Chloro-pyrimidin-4-yl)-2-pyrrolidin-1-yl-benzonitrile (50 mg, 0.18 mmol) was dissolved in NMP (1 mL). 3-Aminobenzamide (100 mg, 0.734 mmol) was added and the mixture was heated at 140° C. in the microwave (300 W, stirring) for 45 minutes. The solvent was evaporated in vacuo (Genevac™). The residue was dissolved in DMSO (1.5 mL) and the crude product purified by reversed phase preparative LC-MS. Fractions containing desired product were combined and the solvents evaporated in vacuo (Genevac™). The title compound was afforded as an off-white solid (15.3 mg, 23%); LC-MS, $R_t$=8.00 min (ANALpH2_MeOH_QC), m/z 400 (MH⁺).

In addition to this procedure similar reactions may alternatively be accomplished by heating at 120-160° C. for 15 to 360 minutes in the microwave, with products purified by either reversed phase preparative LC-MS or flash chromatography on silica. Alternatively similar reactions may also be accomplished using potassium tert-butoxide in THF at reflux for 16 hours in a sealed tube, or potassium carbonate in DMF in a sealed tube at 125° C. for 16 hours.

The compound DMX-1 had an $IC_{50}$ for inhibition of IKKε of <30 nM; and an $IC_{50}$ for inhibition of TBK-1 of <30 nM.

The following compounds were made using analogous chemistry to that described for example DMX-1:

| Structure | Ex. No. | Analytical Data | Inhibition of IKKε $IC_{50}$ | Inhibition of TBK-1 $IC_{50}$ |
|---|---|---|---|---|
| 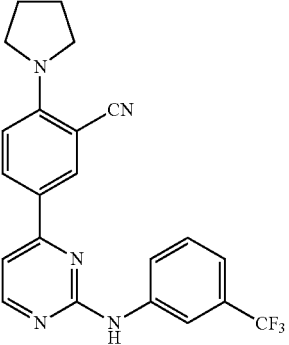 [SMILES: N#Cc1cc(-c2ccnc(Nc3cccc(C(F)(F)F)c3)n2)ccc1N1CCCC1] | DMX-2 | AnalpH2_MeOH_QC; Rt = 9.12 min; m/z 410 (MH+); Pale brown solid. | <9 μM | Not tested |
| 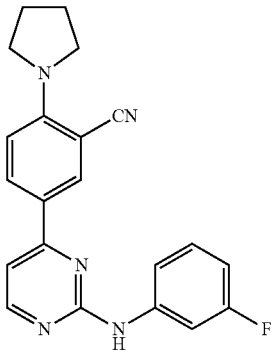 [SMILES: N#Cc1cc(-c2ccnc(Nc3cccc(F)c3)n2)ccc1N1CCCC1] | DMX-3 | AnalpH2_MeOH_QC; Rt = 8.98 min; m/z 360 (MH+) Pale brown solid. | <300 nM | Not tested |
| 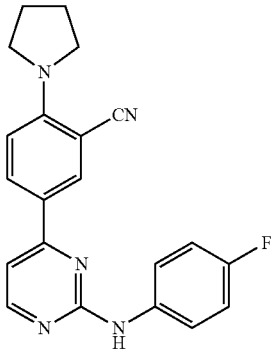 [SMILES: N#Cc1cc(-c2ccnc(Nc3ccc(F)cc3)n2)ccc1N1CCCC1] | DMX-4 | AnalpH2_MeOH_QC; Rt = 8.88 min; m/z 360 (MH+); Pale brown solid. | <300 nM | Not tested |
| 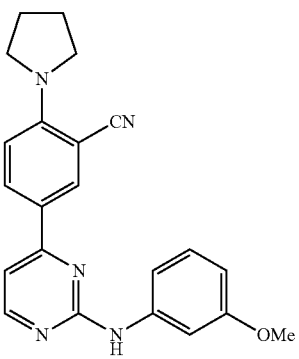 [SMILES: COc1cccc(Nc2nccc(-c3ccc(N4CCCC4)c(C#N)c3)n2)c1] | DMX-5 | AnalpH2_MeOH_QC; Rt = 8.87 min; m/z 372 (MH+); Brown solid. | <30 nM | Not tested |

-continued
| Structure | Ex. No. | Analytical Data | Inhibition of IKKε IC$_{50}$ | Inhibition of TBK-1 IC$_{50}$ |
|---|---|---|---|---|
| 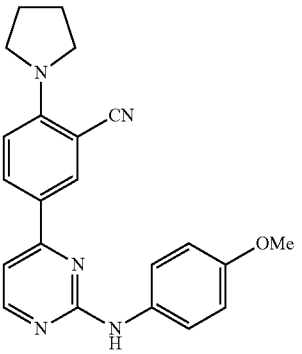 [SMILES: COc1ccc(Nc2nccc(-c3ccc(N4CCCC4)c(C#N)c3)n2)cc1] | DMX-6 | AnalpH2_MeOH_QC; Rt = 8.62 min; m/z 372 (MH$^+$); Brown solid. | <30 nM | Not tested |
| 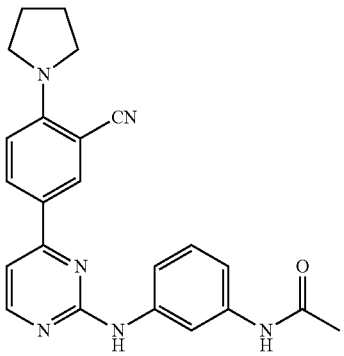 [SMILES: CC(=O)Nc1cccc(Nc2nccc(-c3ccc(N4CCCC4)c(C#N)c3)n2)c1] | DMX-7 | AnalpH2_MeOH_QC; Rt = 8.10 min; m/z 399 (MH$^+$); Pale brown solid. | <30 nM | <30 nM |
| 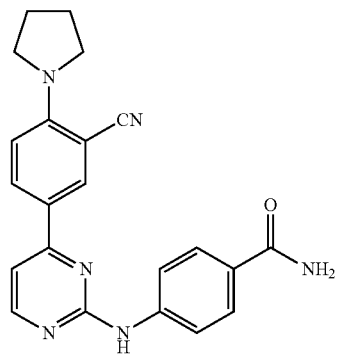 [SMILES: N#Cc1cc(-c2ccnc(Nc3ccc(C(N)=O)cc3)n2)ccc1N1CCCC1] | DMX-8 | AnalpH2_MeOH_QC; Rt = 8.05 min; m/z 385 (MH$^+$); Pale brown solid. | <30 nM | <30 nM |
| 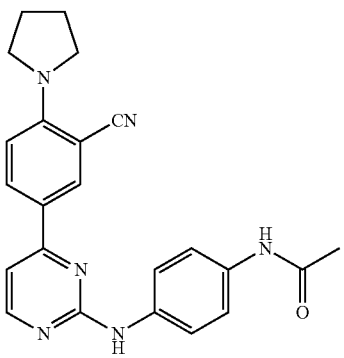 [SMILES: CC(=O)Nc1ccc(Nc2nccc(-c3ccc(N4CCCC4)c(C#N)c3)n2)cc1] | DMX-9 | AnalpH2_MeOH_QC; Rt = 8.08 min; m/z 399 (MH$^+$); Pale brown solid. | <30 nM | <30 nM |

-continued

| Structure | Ex. No. | Analytical Data | Inhibition of IKKEε IC$_{50}$ | Inhibition of TBK-1 IC$_{50}$ |
|---|---|---|---|---|
| 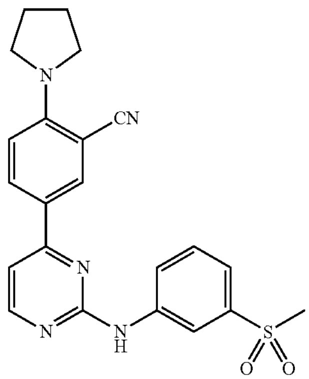 [SMILES: CS(=O)(=O)c1cccc(Nc2nccc(-c3ccc(N4CCCC4)c(C#N)c3)n2)c1] | DMX-10 | AnalpH2_MeOH_QC; Rt = 8.21 min; m/z 420 (MH$^+$); Pale brown solid. | <30 nM | <30 nM |
| 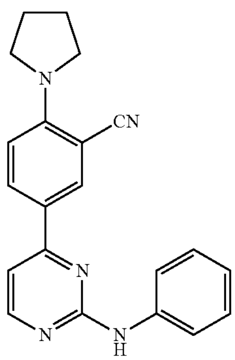 [SMILES: N#Cc1cc(-c2ccnc(Nc3ccccc3)n2)ccc1N1CCCC1] | DMX-11 | AnalpH2_MeOH_QC; Rt = 8.86 min; m/z 342 (MH$^+$); Brown solid. | <9 μM | Not tested |
| 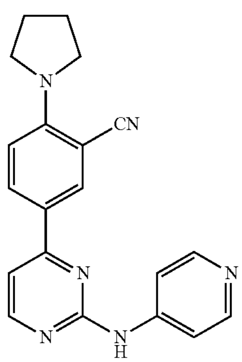 [SMILES: N#Cc1cc(-c2ccnc(Nc3ccncc3)n2)ccc1N1CCCC1] | DMX-12 | AnalpH2_MeOH_QC; Rt = 5.88 min; m/z 343 (MH$^+$); Yellow solid. | <9 μM | Not tested |
| 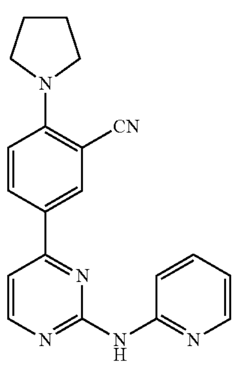 [SMILES: N#Cc1cc(-c2ccnc(Nc3ccccn3)n2)ccc1N1CCCC1] | DMX-13 | AnalpH2_MeOH_QC; Rt = 6.20 min; m/z 343 (MH$^+$); Brown solid. | <9 μM | Not tested |

| Structure | Ex. No. | Analytical Data | Inhibition of IKKε IC$_{50}$ | Inhibition of TBK-1 IC$_{50}$ |
|---|---|---|---|---|
| 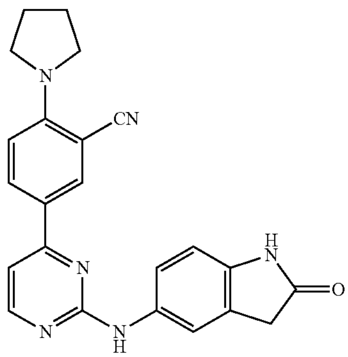 [SMILES: N#Cc1cc(-c2ccnc(Nc3ccc4c(c3)CC(=O)N4)n2)ccc1N1CCCC1] | DMX-14 | AnalpH2_MeOH_QC; Rt = 8.04 min; m/z 397 (MH$^+$); Brown solid. | <30 nM | <30 nM |
| 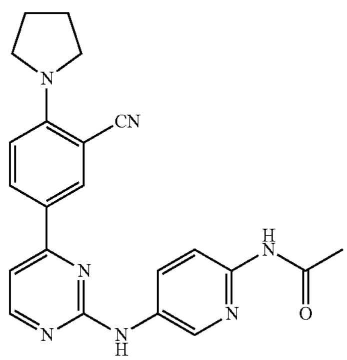 [SMILES: CC(=O)Nc1ccc(Nc2nccc(-c3ccc(N4CCCC4)c(C#N)c3)n2)cn1] | DMX-15 | AnalpH2_MeOH_QC; Rt = 8.10 min; m/z 400 (MH$^+$); Pale brown solid. | <30 nM | <30 nM |
| 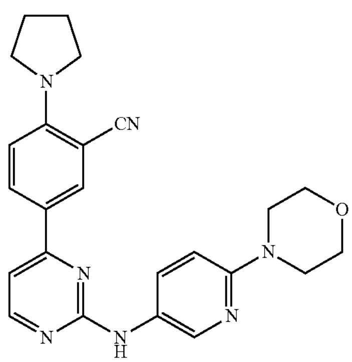 [SMILES: N#Cc1cc(-c2ccnc(Nc3ccc(N4CCOCC4)nc3)n2)ccc1N1CCCC1] | DMX-16 | AnalpH2_MeOH_QC; Rt = 7.56 min; m/z 428 (MH$^+$); Off-white solid. | <30 nM | <30 nM |
| 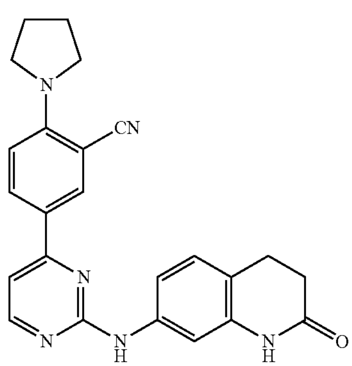 [SMILES: N#Cc1cc(-c2ccnc(Nc3ccc4c(c3)NC(=O)CC4)n2)ccc1N1CCCC1] | DMX-17 | AnalpH2_MeOH_QC; Rt = 8.40 min; m/z 411 (MH$^+$); Pale brown solid. | <30 nM | <30 nM |

-continued
| Structure | Ex. No. | Analytical Data | Inhibition of IKKε IC$_{50}$ | Inhibition of TBK-1 IC$_{50}$ |
|---|---|---|---|---|
| 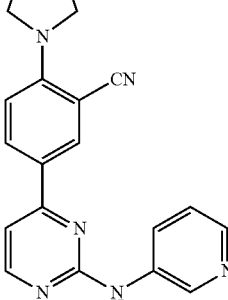 | DMX-18 | AnalpH2_MeOH_QC; Rt = 7.10 min; m/z 343 (MH⁺); Red/brown solid. | <30 nM | Not tested |
| 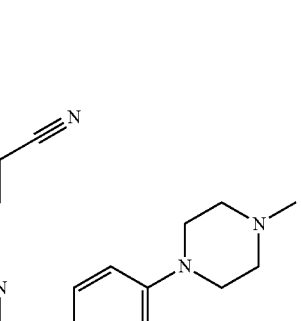 | DMX-19 | Method X; Rt = 2.70 min; m/z 441 (MH⁺); Yellow powder. | <30 nM | <30 nM |
| 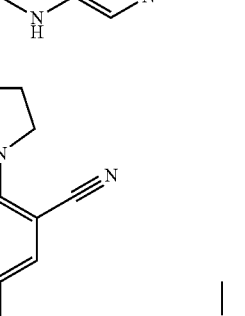 | DMX-20 | Method X; Rt = 2.90 min; m/z 386 (MH⁺); Yellow powder. | <30 nM | <30 nM |
| 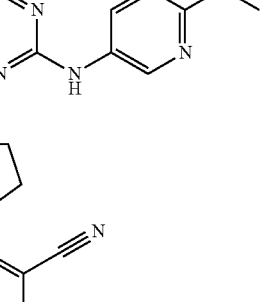 | DMX-21 | Method X; Rt = 3.75 min; m/z 399 (MH⁺); Yellow powder. | <300 nM | <300 nM |

| Structure | Ex. No. | Analytical Data | Inhibition of IKKε IC$_{50}$ | Inhibition of TBK-1 IC$_{50}$ |
|---|---|---|---|---|
| (pyrrolidine-phenyl(CN)-pyrimidine-NH-(1-methylpyrazole)) | DMX-56 | Method X; Rt = 4.13 min; m/z 346 (MH$^+$); Yellow solid. | <30 nM | <30 nM |
| (pyrrolidine-phenyl(CN)-pyrimidine-NH-(1-methylimidazole)) | DMX-57† HCl salt | Method X; Rt = 3.31 min; m/z 346 (MH$^+$); Yellow solid. | <300 nM | <300 nM |
| (pyrrolidine-phenyl(CN)-pyrimidine-NH-(6-methoxypyridine)) | DMX-58 | Method X; Rt = 5.01 min; m/z 373 (MH$^+$); Brown solid. | <30 nM | <30 nM |
| (pyrrolidine-phenyl(CN)-pyrimidine-NH-pyrazole-CH$_2$CONH$_2$) | DMX-59 | Method Y; Rt = 1.65 min; m/z 389 (MH$^+$); White solid. | <300 nM | <300 nM |

| Structure | Ex. No. | Analytical Data | Inhibition of IKKEε $IC_{50}$ | Inhibition of TBK-1 $IC_{50}$ |
|---|---|---|---|---|
| 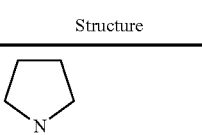 | DMX-60 | Method I; Rt = 2.46 min; m/z 346 (MH$^+$); Pale brown solid. | <300 nM | <300 nM |

†The hydrochloride salt was prepared from the parent free base by dissolving the latter in 2M HCl-diethyl ether and collecting the precipitated hydrochloride salt by filtration under reduced pressure (the compound was screened as a hydrochloride salt).

Example DMX-22

Synthesis of pyrrolidine-1-carboxylic acid {3-[4-(3-cyano-4-pyrrolidin-1-yl-phenyl)-pyrimidin-2-ylamino]phenyl}-amide Synthesis of pyrrolidine-1-carboxylic acid (3-nitrophenyl)-amide

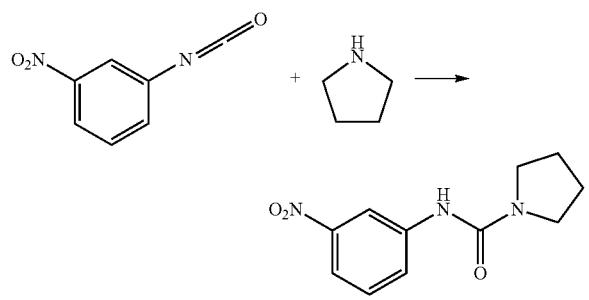

Pyrrolidine (1.5 mL, 18.3 mmol) was added to a stirred solution of 3-nitrophenyl isocyanate (1.5 g, 9.14 mmol) in anhydrous THF (60 mL) and the mixture stirred at reflux for 1 hour. The solvent was evaporated in vacuo. The crude product was then purified by column chromatography (Flashmaster, 40-63 mesh silica gel, 50% isohexane-EtOAc) to provide the title compound as an off white solid (1.85 g, 86%); LC-MS, $R_t$=2.80 min (MeOH-FA), m/z 236 (MH$^+$).

Synthesis of pyrrolidine-1-carboxylic acid (3-amino-phenyl)-amide

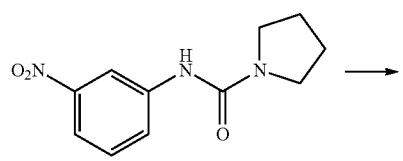

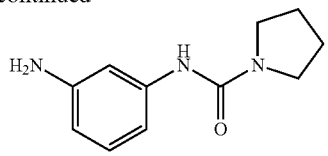

Pyrrolidine-1-carboxylic acid (3-nitro-phenyl)-amide (850 mg, 3.40 mmol) was dissolved in 1:1 MeOH-EtOAc (100 mL). Raney®-Nickel was added (3 full spatulas) followed by hydrazine monohydrate (1.70 g, 34.0 mmol) over a 5 minute period. The reaction mixture was stirred at rt for 16 hours then filtered through celite, washing the precipitate with EtOAc (10×10 mL). The filtrate was evaporated in vacuo and the residue dissolved in EtOAc (50 mL). The solution was washed with saturated brine solution (2×50 mL), dried (Na$_2$SO$_4$), filtered, and the solvent evaporated in vacuo. The crude product was then purified by column chromatography (Flashmaster, 40-63 mesh silica gel, EtOAc→10% MeOH-EtOAc) to provide the title compound as a pale yellow solid (1.29 g, 92%); LC-MS, $R_t$=0.99 min (MeOH-FA), m/z 206 (MH$^+$).

Pyrrolidine-1-carboxylic acid {3-[4-(3-cyano-4-pyrrolidin-1-yl-phenyl)-pyrimidin-2-ylamino]-phenyl}-amide (DMX-22)

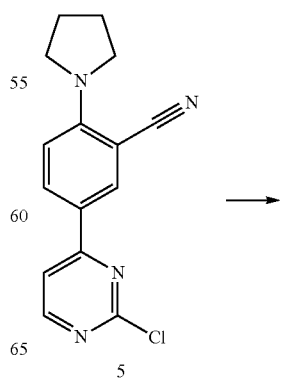

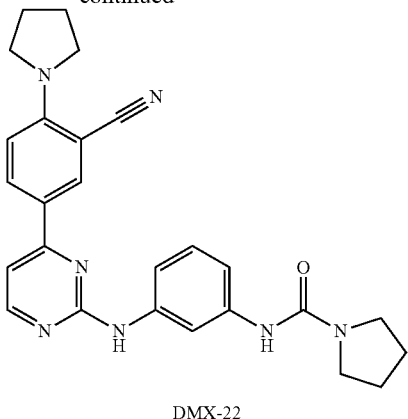

DMX-22

5-(2-Chloro-pyrimidin-4-yl)-2-pyrrolidin-1-yl-benzonitrile (40 mg, 0.141 mmol), pyrrolidine-1-carboxylic acid (3-amino-phenyl)-amide (29 mg, 0.141 mmol), Pd$_2$(dba)$_3$ (6.4 mg, 0.007 mmol, 5 mol %), 2-dicyclohexylphosphino-2'-(N,N-dimethylaminobiphenyl) (55.5 mg, 0.141 mmol) and NaO$^t$Bu (20.3 mg, 0.211 mmol) were dissolved in 1,4-dioxane (1 mL) and the mixture heated at 100° C. in the microwave (300 W, stirring) for 10 minutes. The mixture was diluted with H$_2$O (10 mL) and EtOAc (30 mL) and the layers separated. The aqueous phase was extracted with EtOAc (20 mL) and the combined organics dried (MgSO$_4$), filtered and the solvent evaporated in vacuo. The mixture was dissolved in DMSO (1.5 mL) and the crude product purified by reversed phase preparative LC-MS. Fractions containing desired product were combined and the solvent evaporated in vacuo. The title compound was afforded as a yellow solid (13.1 mg, 21%); LC-MS, R$_t$=6.50 min (ANALpH2_MeOH_QC), m/z 453 (MH$^+$).

In addition to this procedure similar reactions may also be accomplished by stirring the reactants with sodium tert-butoxide, Dave-Phos, Pd$_2$(dba)$_3$ and 1,4-dioxane in a sealed tube at 70-100° C. for 1 hour.

DMX-22 had an 1050 for inhibition of IKKε of <30 nM, and an IC50 for inhibition of TBK-1 of <30 nM.

The following compounds were made using analogous chemistry to that described for Example DMX-22:

| Structure | Example | Analytical Data | Inhibition of IKKε IC$_{50}$ | Inhibition of TBK-1 IC$_{50}$ |
|---|---|---|---|---|
| 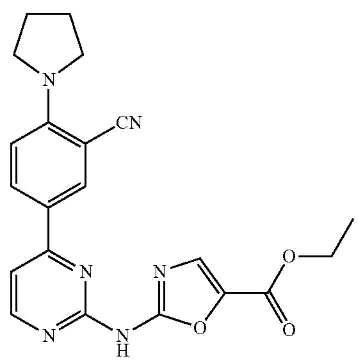 [SMILES: CCOC(=O)c1cnc(Nc2nccc(-c3ccc(N4CCCC4)c(C#N)c3)n2)o1] | DMX-23 | MeOH—FA; Rt = 3.09 min; m/z 405 (MH$^+$); Brown solid. | Not tested | Not tested |
| 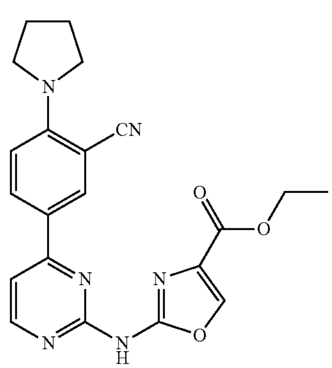 [SMILES: CCOC(=O)c1coc(Nc2nccc(-c3ccc(N4CCCC4)c(C#N)c3)n2)n1] | DMX-24 | MeOH—FA; Rt = 3.01 min; m/z 405 (MH$^+$); Yellow solid. | Not tested | Not tested |

-continued

| Structure | Example | Analytical Data | Inhibition of IKKε IC$_{50}$ | Inhibition of TBK-1 IC$_{50}$ |
|---|---|---|---|---|
| 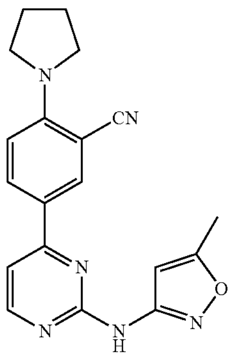 [SMILES: Cc1cc(Nc2nccc(-c3ccc(N4CCCC4)c(C#N)c3)n2)no1] | DMX-25** | AnalpH2_MeOH_QC; Rt = 7.28 min; m/z 347 (MH$^+$); Yellow solid. | <9 μM | Not tested |
| 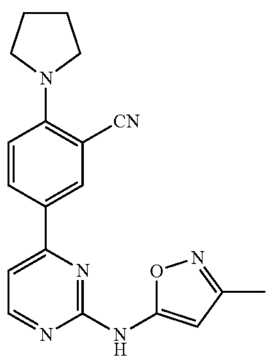 [SMILES: Cc1cc(Nc2nccc(-c3ccc(N4CCCC4)c(C#N)c3)n2)on1] | DMX-26** | AnalpH2_MeOH_QC; Rt = 8.51 min; m/z 347 (MH$^+$); Yellow solid. | <300 nM | <300 nM |
| 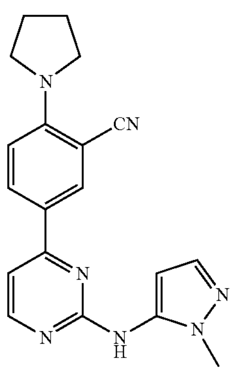 [SMILES: Cn1nccc1Nc1nccc(-c2ccc(N3CCCC3)c(C#N)c2)n1] | DMX-27** | AnalpH2_MeOH_QC; Rt = 8.06 min; m/z 346 (MH$^+$); Yellow solid. | <300 nM | <30 nM |
| 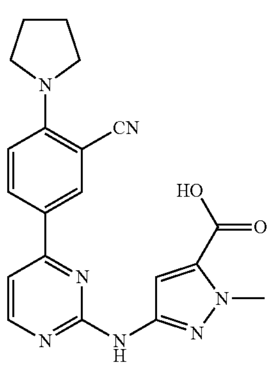 [SMILES: Cn1nc(Nc2nccc(-c3ccc(N4CCCC4)c(C#N)c3)n2)cc1C(=O)O] | DMX-28 | MeOH—FA; Rt = 3.00 min; m/z 390 (MH$^+$); Yellow/brown solid. | Not tested | Not tested |

-continued
| Structure | Example | Analytical Data | Inhibition of IKKε IC$_{50}$ | Inhibition of TBK-1 IC$_{50}$ |
|---|---|---|---|---|
| 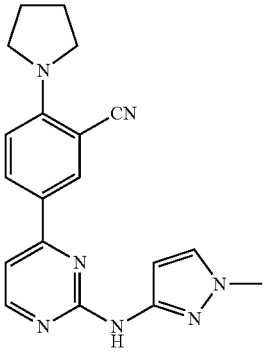 [SMILES: Cn1ccc(Nc2nccc(-c3ccc(N4CCCC4)c(C#N)c3)n2)n1] | DMX-29 | AnalpH2_MeOH_QC; Rt = 7.58 min; m/z 346 (MH$^+$); Red/orange solid. | <300 nM | <300 nM |
| 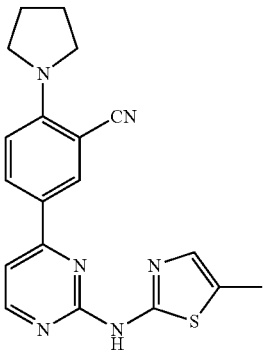 [SMILES: Cc1cnc(Nc2nccc(-c3ccc(N4CCCC4)c(C#N)c3)n2)s1] | DMX-30 | AnalpH2_MeOH_QC; Rt = 8.65 min; m/z 363 (MH$^+$); Orange/yellow solid. | <9 μM | Not tested |
| 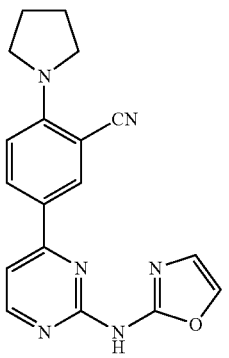 [SMILES: N#Cc1cc(-c2ccnc(Nc3ncco3)n2)ccc1N1CCCC1] | DMX-31 | AnalpH2_MeOH_QC; Rt = 8.62 min; m/z 363 (MH$^+$); Yellow solid. | <9 μM | Not tested |
| 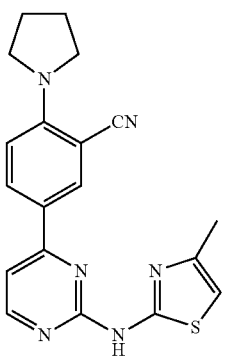 [SMILES: Cc1csc(Nc2nccc(-c3ccc(N4CCCC4)c(C#N)c3)n2)n1] | DMX-32 | AnalpH2_MeOH_QC; Rt = 8.62 min; m/z 363 (MH$^+$); Yellow solid. | <9 μM | Not tested |

| Structure | Example | Analytical Data | Inhibition of IKKε IC$_{50}$ | Inhibition of TBK-1 IC$_{50}$ |
|---|---|---|---|---|
| 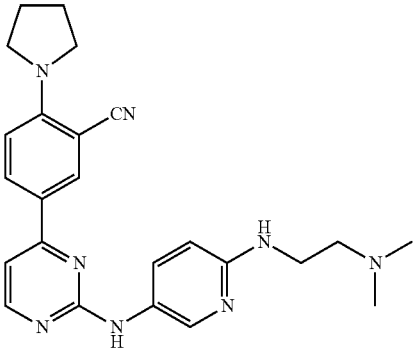 [SMILES: CN(C)CCNc1ccc(Nc2nccc(-c3ccc(N4CCCC4)c(C#N)c3)n2)cn1] | DMX-33* | Method Y; Rt = 2.73 min; m/z 429 (MH$^+$); Pale yellow powder. | <30 nM | <30 nM |
| 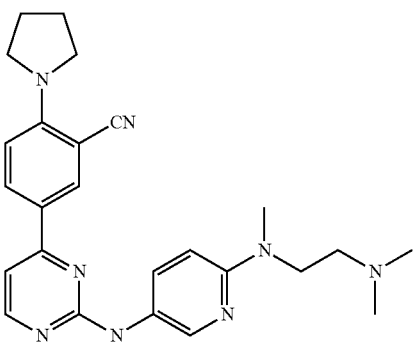 | DMX-34 | Method Z; Rt = 1.819 min; m/z 443 (MH$^+$); Yellow powder. | <30 nM | <30 nM |
| 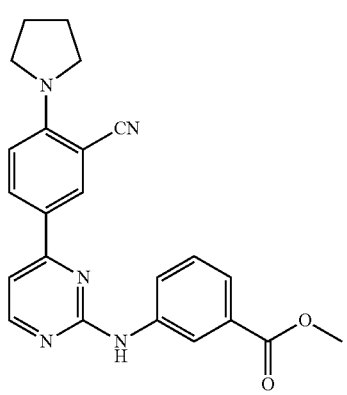 [SMILES: COC(=O)c1cccc(Nc2nccc(-c3ccc(N4CCCC4)c(C#N)c3)n2)c1] | DMX-35 | — | Not tested | Not tested |
| 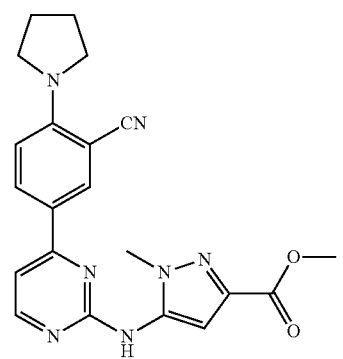 [SMILES: COC(=O)c1cc(Nc2nccc(-c3ccc(N4CCCC4)c(C#N)c3)n2)n(C)n1] | DMX-36* | — | Not tested | Not tested |

| Structure | Example | Analytical Data | Inhibition of IKKε IC$_{50}$ | Inhibition of TBK-1 IC$_{50}$ |
|---|---|---|---|---|
| (structure with pyrrolidine, CN, pyrimidine, N-methylacetamide phenyl) | DMX-37 | Method X; Rt = 4.20 min; m/z 413 (MH$^+$); Yellow powder. | <30 nM | <30 nM |
| (structure with pyrrolidine, CN, pyrimidine, pyridyl-O-ethyl-NMe$_2$) | DMX-61 | Method X; Rt = 3.31 min; m/z 430 (MH$^+$); Off-white solid. | <30 nM | <30 nM |

*Amines used for coupling with intermediate 5 were synthesised as they were not readily available from commercial suppliers.

For examples DMX-33 and DMX-34 the requisite amines were made in two steps from 2-chloro-5-nitro-pyridine by displacement of the 2-chloro group with the corresponding ethylene diamine, using triethylamine in acetonitrile at rt. This was followed by reduction of the nitro group with either Raney ®-Nickel and hydrazine or hydrogenation over 10% Pd—C.

For example DMX-36 the requisite amine was made in 5 steps from 3,5-Dimethyl-1H- pyrazole according to procedures described by Lee et al., *J. Org. Chem*, 1989, 428-431.

**These compounds were synthesised from the 2-iodoanalogue of compound 5 using analogous conditions. This was in turn made using an analogous route to compound 5 starting from 2,4-diiodopyrimidine.

In addition some of the compounds in the above table were used for the synthesis of further analogues.

Examples DMX-38, 39 and 41 were synthesised by amidation of the respective ethyl or methyl esters, by heating with ammonia in methanol. DMX-40 was synthesised from the carboxylic acid DMX-28 by initial conversion to the acid chloride followed by amidation using conditions that are common in the art. DMX-42 was prepared by hydrolysis of the methyl ester DMX-35 and examples DMX43-45 were prepared from DMX-42 using amide coupling conditions that are common in the art.

| Structure | Starting Material | Example | Analytical Data | Inhibition of IKKε IC$_{50}$ | Inhibition of IKKε IC$_{50}$ |
|---|---|---|---|---|---|
| (structure with pyrrolidine, CN-phenyl, pyrimidine, oxazole carboxamide) | DMX-23 | DMX-38 | AnalpH2_MeOH_QC; Rt = 7.55 min; m/z 376 (MH$^+$); Yellow/brown solid. | <9 μM | Not tested |

-continued

| Structure | Starting Material | Example | Analytical Data | Inhibition of IKKε IC$_{50}$ | Inhibition of IKKε IC$_{50}$ |
|---|---|---|---|---|---|
| (pyrrolidine-phenyl(CN)-pyrimidine-NH-oxazole-carboxamide) | DMX-24 | DMX-39 | AnalpH2_MeOH_QC; Rt = 7.70 min; m/z 376 (MH$^+$); Yellow solid. | <9 μM | Not tested |
| (pyrrolidine-phenyl(CN)-pyrimidine-NH-(1-methylpyrazole-5-carboxamide)) | DMX-28 | DMX-40 | AnalpH2_MeOH_QC; Rt = 7.48 min; m/z 389 (MH$^+$); Yellow solid. | <300 nM | <3 μM |
| (pyrrolidine-phenyl(CN)-pyrimidine-NH-(1-methylpyrazole-3-carboxamide)) | DMX-36 | DMX-41 | Method X; Rt = 3.49 min; m/z 389 (MH$^+$); Pale yellow powder. | <300 nM | <300 nM |
| (pyrrolidine-phenyl(CN)-pyrimidine-NH-benzoic acid) | DMX-35 | DMX-42 | Method-FA Rt = 3.09 min; m/z 386 (MH$^+$) yellow powder | <30 nM | <30 nM |

-continued

| Structure | Starting Material | Example | Analytical Data | Inhibition of IKKε IC$_{50}$ | Inhibition of IKKε IC$_{50}$ |
|---|---|---|---|---|---|
| (structure with pyrrolidine, CN, pyrimidine-NH-phenyl-C(O)-N-methylpiperazine) | DMX-42 | DMX-43 | Method Y; Rt = 1.61 min; m/z 468 (MH$^+$); Pale yellow powder. | <30 nM | <30 nM |
| (structure with pyrrolidine, CN, pyrimidine-NH-phenyl-C(O)NH-N-methylpiperidine) | DMX-42 | DMX-44 | Method Y; Rt = 1.62 min; m/z 482 (MH$^+$); Off-white powder. | <30 nM | <30 nM |
| (structure with pyrrolidine, CN, pyrimidine-NH-phenyl-C(O)NH-CH$_2$CH$_2$-N(CH$_3$)$_2$) | DMX-42 | DMX-45 | Method Y; Rt = 1.64 min; m/z 456 (MH$^+$); Pale yellow powder. | <30 nM | <30 nM |

Additional compounds as shown in the following table were synthesised by methods analogous to methods above:

| Structure | Example | Analytical Data | Inhibition of IKKε IC$_{50}$ | Inhibition of TBK-1 IC$_{50}$ |
|---|---|---|---|---|
| (morpholine-substituted structure) | DMX-46 (method see DMX-1) | Method X; Rt = 3.15 min; m/z 416 (MH$^+$); Pale yellow powder. | <300 nM | <30 nM |
| (N-methylpiperazine-substituted structure) | DMX-47 (method see DMX-22) | Method B; Rt = 2.599 min; m/z 429 (MH$^+$); Pale orange powder. | <300 nM | <300 nM |
| (3-hydroxypyrrolidine-substituted structure) | DMX-48 (method see DMX-1) | Method X; Rt = 2.80 min, m/z 416 (MH$^+$); Yellow powder. | <30 nM | <30 nM |

| Structure | Example | Analytical Data | Inhibition of IKKε IC$_{50}$ | Inhibition of TBK-1 IC$_{50}$ |
|---|---|---|---|---|
| 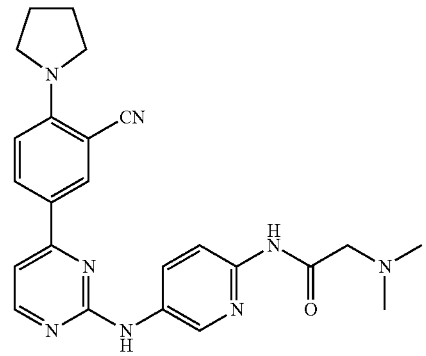 [SMILES: CN(C)CC(=O)Nc1ccc(Nc2nccc(-c3ccc(N4CCCC4)c(C#N)c3)n2)cn1] | DMX-49* (method see DMX-22) | Method D Rt = 2.89 min m/z 443 (MH+); pale yellow powder | <30 nM | <30 nM |

*Amines used for coupling with intermediate 5 were synthesised as they were not readily available from commercial suppliers.

For example DMX-49 the requisite amine was made in 3 steps from 5-nitro-pyridin-2-ylamine. This was first coupled with chloroacetyl chloride in refluxing THF using triethylamine as a base, followed by displacement of the chloride with dimethylamine in acetonitrile using potassium carbonate as base. The nitro group was subsequently reduced under hydrogenation conditions at atmospheric pressure using 10% Pd/C as catalyst to yield the desired amine.

An alternative route via intermediate 6 was followed for the synthesis of some compounds. Intermediate 6 was synthesised according to patent application WO2009/032861.

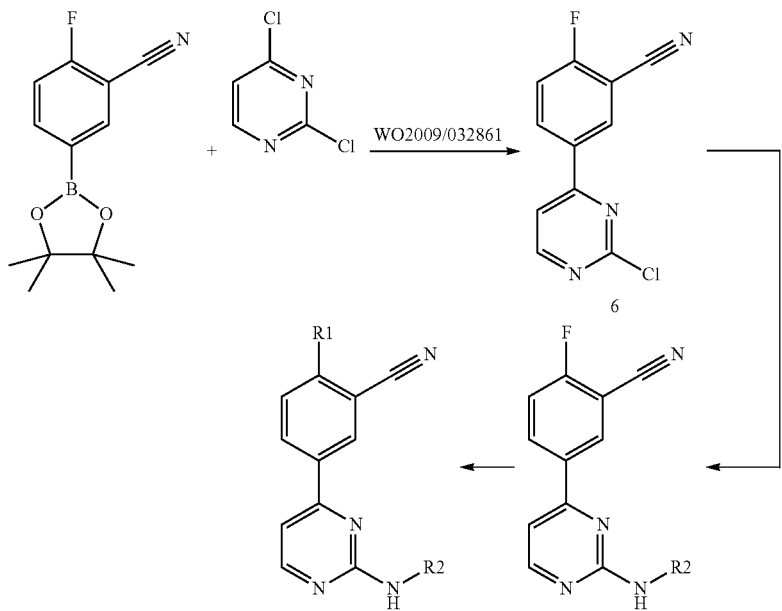

Example DMX-50

Synthesis of 1-{4-[2-(6-Acetylamine-pyridin-3-ylamino)-pyrimidin-4-yl]-2-cyano-phenyl}-piperidine-4-carboxylic acid amide N-{5-[4-(3-Cyano-4-fluoro-phenyl)-pyrimidin-2-ylamino]-pyridin-2-yl}-acetamide A mixture of Compound 6 (500 mg, 2.14 mmol), N-(5-Amino-pyridin-2-yl)-acetamide (390 mg, 2.57 mmol), NaOt-Bu (309 mg, 3.21 mmol) and Dave-phos (253 mg, 0.64 mmol) in 1,4-dioxane (20 mL) was degassed with argon for 30 min, Pd$_2$(dba)$_3$ (98 mg, 0.10 mmol) was added and again degassed for 10 min, the resulting suspension was heated to 90° C. in a microwave for 20 min. The reaction mixture was filtered through a celite bed and the filtrate was concentrated in vacuo to provide the crude compound which was purified by column chromatography (Silica gel 100-200 mesh, 0-2% MeOH/CHCl$_3$) to afford N-{5-[4-(3-Cyano-4-fluoro-phenyl)-pyrimidin-2-ylamino]-pyridin-2-yl}-acetamide (260 mg, 34%) as a brown solid. (TLC system: 10% CH$_3$OHCHCl$_3$, R$_f$=0.3).

In addition to this procedure similar reactions may also be accomplished by stirring in 1,4-dioxane in a sealed tube at 110° C. for 1-5 hours; alternatively similar reactions may be performed using Xantphos, Pd$_2$(dba)$_3$, and Cs$_2$CO$_3$ in 1,4-dioxane in a sealed tube at reflux for 1 hour.

1-{4-[2-(6-Acetylamino-pyridin-3-ylamino)-pyrimidin-4-yl]-2-cyano-phenyl}-piperidine-4-carboxylic acid amide DMX-50

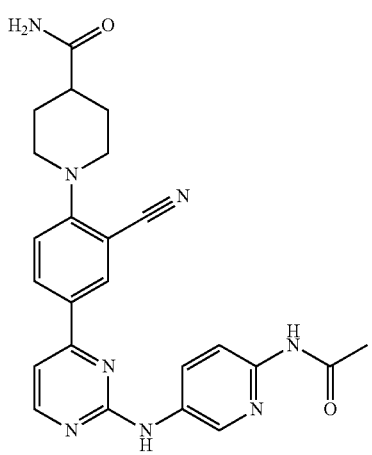

DMX-50

A stirred solution of N-{5-[4-(3-Cyano-4-fluoro-phenyl)-pyrimidin-2-ylamino]-pyridin-2-yl}-acetamide (100 mg, 0.28 mmol) and piperidine-4-carboxylic acid amide in n-butanol (5 mL) was heated to 115° C. in a sealed tube for 48 h. The solvent was evaporated to obtain the crude compound. The crude compound was purified by preparative-HPLC to obtain the desired product as pale yellow powder (38 mg, 29%); LC-MS, Rt,=2.96 min (Method C), m/z 457 (MH$^+$). In addition to this procedure similar reactions may also be accomplished at 110° for 16-120 h. Purification may be by preparative-HPLC or flash column chromatography.

In addition if the amine reagent is in salt form then these reactions may be accomplished with CsCO$_3$ in DMF at 120° C. in a sealed tube for 24 hours, or CsCO$_3$ in 1,4-dioxane at 100° C. in a sealed tube for 16-24 hours, or K$_2$CO$_3$ in DMF at 120° C. in a sealed tube for 24 hours, or potassium tert-butoxide in 1,4-dioxane at 100° C. in a sealed tube for 24 hours. Purification may be by preparative-HPLC or flash column chromatography.

DMX 50 had an IC$_{50}$ for inhibition of IKKε of <30 nM; and an IC$_{50}$ for inhibition of TBK-1 of <300 nM.

The following compounds were made using analogous chemistry to that described for example DMX-50:

| Structure | Example | Analytical Data | Inhibition of IKKε IC$_{50}$ | Inhibition of TBK-1 IC$_{50}$ |
|---|---|---|---|---|
| 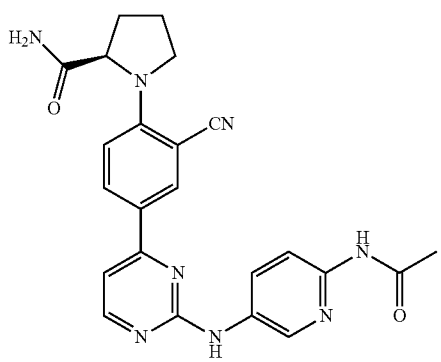 [SMILES: CC(=O)Nc1ccc(Nc2nccc(-c3ccc(N4CCC[C@@H]4C(N)=O)c(C#N)c3)n2)cn1] | DMX-51 | Method C; Rt = 2.53 min; m/z 443 (MH$^+$); Pale brown powder. | <300 nM | <300 nM |
| 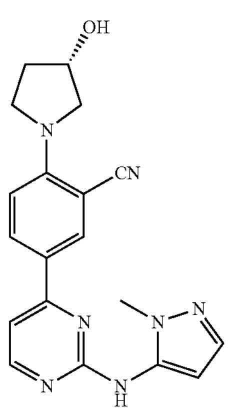 [SMILES: Cn1nccc1Nc1nccc(-c2ccc(N3CC[C@H](O)C3)c(C#N)c2)n1] | DMX-52 | Method D; Rt = 3.51 min; m/z 362 (MH$^+$); Yellow powder | <300 nM | <300 nM |

-continued
| Structure | Example | Analytical Data | Inhibition of IKKε IC$_{50}$ | Inhibition of TBK-1 IC$_{50}$ |
|---|---|---|---|---|
| 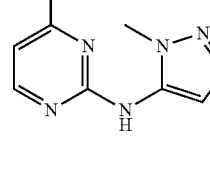 | DMX-53 | Method E; Rt = 2.59 min; m/z 389 (MH$^+$) Pale yellow powder | <300 nM | <3 μM |
| 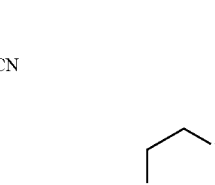 | DMX-54 | Method D; Rt = 2.71 min m/z 457 (MH$^+$) Yellow powder | <30 nM | <30 nM |
| 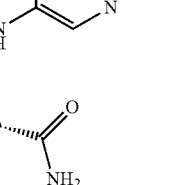 | DMX-55 | Method D; Rt = 2.59 min m/z 484 (MH$^+$) Yellow powder | <30 nM | <30 nM |
| 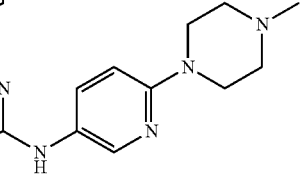 | DMX-62 | Method Y; Rt = 1.01 min; m/z 445 (MH$^+$); Pale yellow solid. | <30 nM | <30 nM |

| Structure | Example | Analytical Data | Inhibition of IKKε IC$_{50}$ | Inhibition of TBK-1 IC$_{50}$ |
|---|---|---|---|---|
| (structure) | DMX-63 | Method Y; Rt = 1.47 min; m/z 443 (MH$^+$); Brown solid. | <30 nM | <30 nM |
| (structure) | DMX-64 | Method X; Rt = 2.59 min; m/z 486 (MH$^+$); Yellow solid. | <30 nM | <300 nM |
| (structure) | DMX-65 | Method Y; Rt = 1.00 min; m/z 459 (MH$^+$); Brown solid. | <300 nM | <300 nM |

-continued

| Structure | Example | Analytical Data | Inhibition of IKKε IC$_{50}$ | Inhibition of TBK-1 IC$_{50}$ |
|---|---|---|---|---|
| 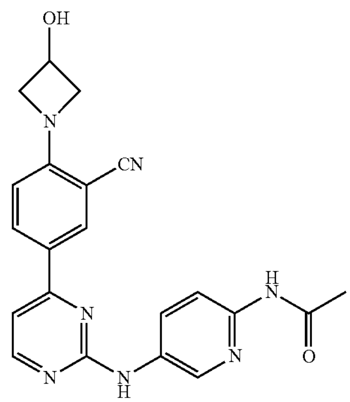 [SMILES: CC(=O)Nc1ccc(Nc2nccc(-c3ccc(N4CC(O)C4)c(C#N)c3)n2)cn1] | DMX-66 | Method F; Rt = 1.71 min; m/z 402 (MH$^+$); Yellow powder. | <30 nM | <30 nM |
| 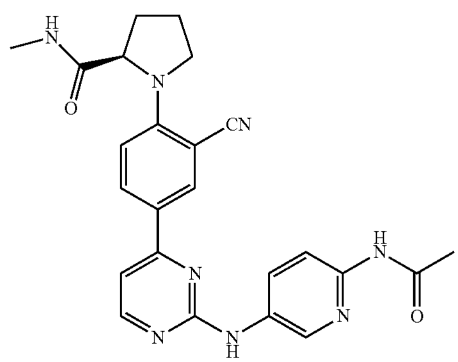 [SMILES: CNC(=O)[C@H]1CCCN1c1ccc(-c2ccnc(Nc3ccc(NC(C)=O)nc3)n2)cc1C#N] | DMX-67* | Method Y; Rt = 1.48 min; m/z 457 (MH$^+$); Yellow powder. | <9 μM | <9 μM |
| 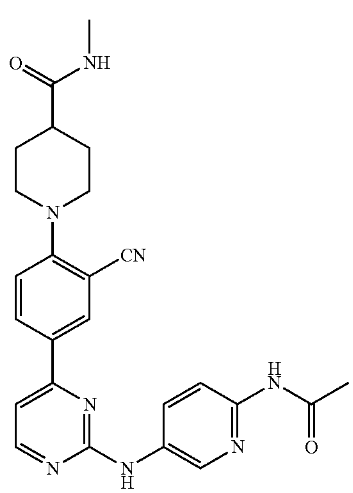 [SMILES: CNC(=O)C1CCN(c2ccc(-c3ccnc(Nc4ccc(NC(C)=O)nc4)n3)cc2C#N)CC1] | DMX-68 | Method G; Rt = 1.21 min; m/z 471 (MH$^+$); Yellow powder. | <300 nM | <300 nM |

| Structure | Example | Analytical Data | Inhibition of IKKε IC$_{50}$ | Inhibition of TBK-1 IC$_{50}$ |
|---|---|---|---|---|
| 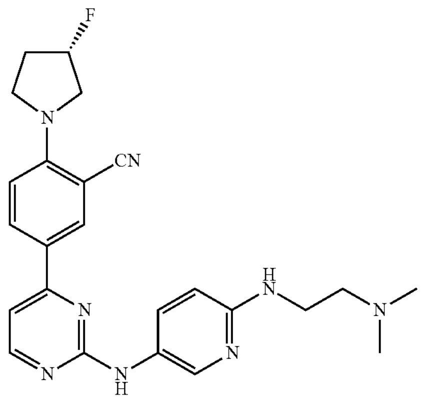 [SMILES: CN(C)CCNc1ccc(Nc2nccc(-c3ccc(N4CC[C@H](F)C4)c(C#N)c3)n2)cn1] | DMX-69 | Method G; Rt = 1.13 min; m/z 447 (MH$^+$); Green/brown solid. | <30 nM | <30 nM |
| 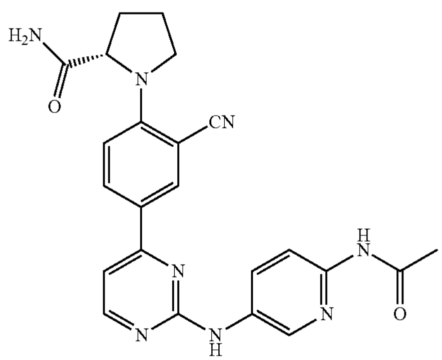 [SMILES: CC(=O)Nc1ccc(Nc2nccc(-c3ccc(N4CCC[C@H]4C(N)=O)c(C#N)c3)n2)cn1] | DMX-70 | Method Y; Rt = 1.52 min; m/z 443 (MH$^+$); Yellow solid. | <300 nM | <300 nM |
| 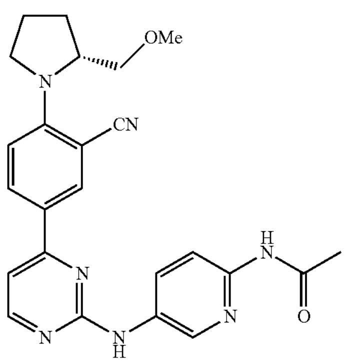 [SMILES: COC[C@H]1CCCN1c1ccc(-c2ccnc(Nc3ccc(NC(C)=O)nc3)n2)cc1C#N] | DMX-71 | Method Y; Rt = 2.12 min; m/z 444 (MH$^+$); Pale brown solid. | <30 nM | <30 nM |
| 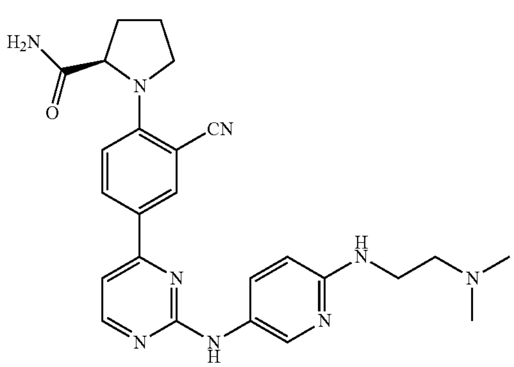 [SMILES: CN(C)CCNc1ccc(Nc2nccc(-c3ccc(N4CCC[C@@H]4C(N)=O)c(C#N)c3)n2)cn1] | DMX-72** | Method Y; Rt = 1.88 min; m/z 472 (MH$^+$); Brown solid. | <300 nM | <300 nM |

| Structure | Example | Analytical Data | Inhibition of IKKε IC$_{50}$ | Inhibition of TBK-1 IC$_{50}$ |
|---|---|---|---|---|
| 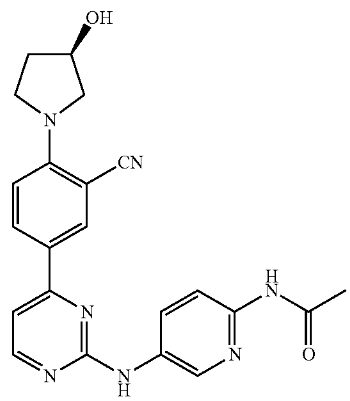 [SMILES: CC(=O)Nc1ccc(Nc2nccc(-c3ccc(N4CC[C@@H](O)C4)c(C#N)c3)n2)cn1] | DMX-73 | Method Y; Rt = 1.37 min; m/z 416 (MH⁺); Brown solid. | <30 nM | <30 nM |
| 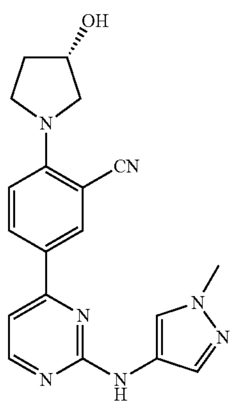 [SMILES: Cn1cc(Nc2nccc(-c3ccc(N4CC[C@H](O)C4)c(C#N)c3)n2)cn1] | DMX-74 | Method Y; Rt = 1.51 min; m/z 362 (MH⁺); Off-white solid. | <30 nM | <30 nM |
| 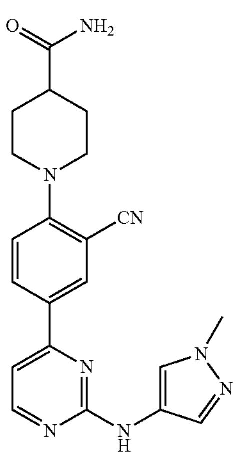 [SMILES: Cn1cc(Nc2nccc(-c3ccc(N4CCC(C(N)=O)CC4)c(C#N)c3)n2)cn1] | DMX-75 | Method Y; Rt = 1.30 min; m/z 403 (MH⁺); Off-white solid. | <30 nM | <300 nM |

-continued

| Structure | Example | Analytical Data | Inhibition of IKKε IC$_{50}$ | Inhibition of TBK-1 IC$_{50}$ |
|---|---|---|---|---|
| 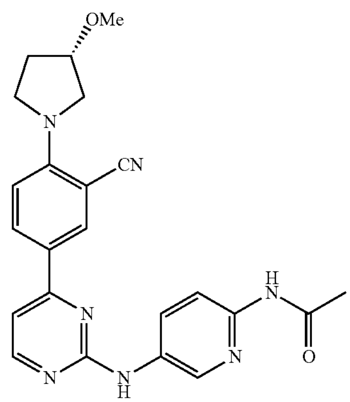 [SMILES: CO[C@H]1CCN(c2ccc(-c3ccnc(Nc4ccc(NC(C)=O)nc4)n3)cc2C#N)C1] | DMX-76 | Method Y; Rt = 1.59 min; m/z 430 (MH$^+$); Yellow solid. | <30 nM | <30 nM |
| 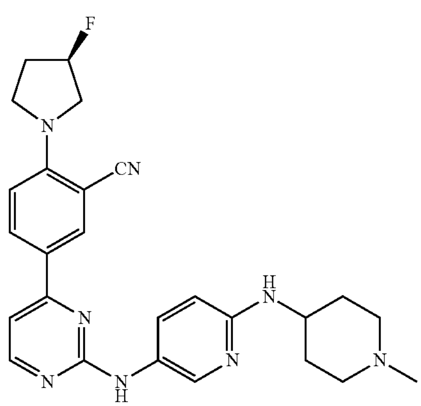 [SMILES: CN1CCC(Nc2ccc(Nc3nccc(-c4ccc(N5CC[C@@H](F)C5)c(C#N)c4)n3)cn2)CC1] | DMX-77** | Method Y; Rt = 1.38 min; m/z 473 (MH$^+$); Pale yellow solid. | <30 nM | <30 nM |
| 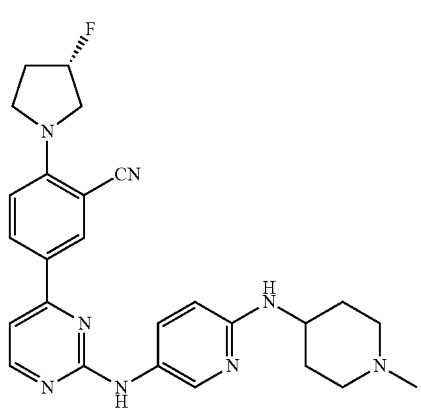 [SMILES: CN1CCC(Nc2ccc(Nc3nccc(-c4ccc(N5CC[C@H](F)C5)c(C#N)c4)n3)cn2)CC1] | DMX-78** | Method Y; Rt = 1.31 min; m/z 473 (MH$^+$); Pale yellow solid. | <30 nM | <30 nM |

| Structure | Example | Analytical Data | Inhibition of IKKε IC$_{50}$ | Inhibition of TBK-1 IC$_{50}$ |
|---|---|---|---|---|
| 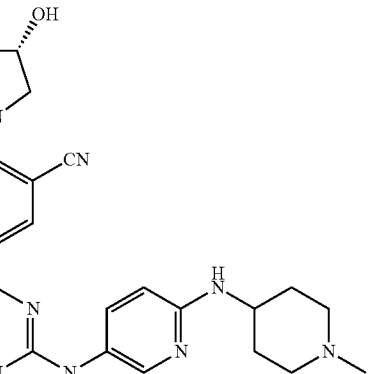 | DMX-79** | Method Y; Rt = 1.02 min; m/z 471 (MH+); Pale brown solid. | <30 nM | <30 nM |
| 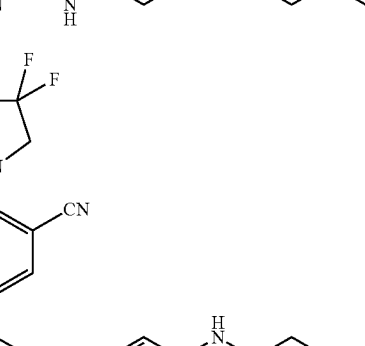 | DMX-80 | Method Y; Rt = 1.45 min; m/z 491 (MH+); Yellow solid. | <30 nM | <30 nM |

*For example DMX-67 the requisite intermediate amine for R1 was prepared using standard literature procedures from D-proline. This material was Boc protected using (Boc)$_2$O, subsequent conversion to the methyl amide was achieved using isobutyl chloroformate and NMM. The final Boc deprotection step with 4N HCl-dioxane furnished the desired amine. This is depicted in the scheme below.

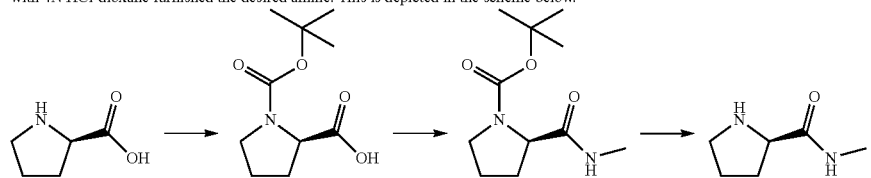

**For the following examples the requisite amines (R$^2$NH$_2$) for use in the Buchwald-Hartwig couplings were not readily available from commercial suppliers and were therefore synthesised.
For examples DMX 77-80 the requisite amine was made in two steps from 2-chloro-5-nitro-pyridine by displacement of the 2-chloro group with 1-methylpiperidin-4y1-amine using potassium carbonate in acetonitrile at reflux. This was followed by reduction of the nitro group with Raney ®-Nickel and hydrazine monohydrate, For example DMX-69 the requisite amine was made as described for example DMX-33.

The invention claimed is:

1. A compound of the general formula I:

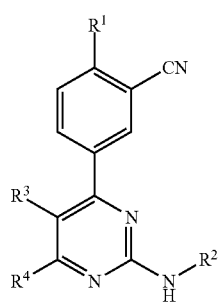

in which:

R$^1$ represents an aliphatic heterocyclyl group having 4, 5, 6 or 7 ring atoms, bonded to the phenyl group shown in formula I through a ring nitrogen atom, and optionally substituted by one or more substituents selected from halogen atoms; OH; =O; C$_{1-4}$alkyl, C$_{1-4}$alkoxy, C$_{1-4}$alkoxyC$_{1-4}$alkyl, C$_{2-4}$alkenyl and C$_{2-4}$alkynyl groups, each optionally substituted by one or more substituents independently selected from halogen atoms and NR$^a$R$^b$ groups; NO$_2$; CN; NR$^a$R$^b$; COR$^c$; O.CO.R$^c$; CO$_2$R$^a$; NR$^a$.COR$^c$;
NR$^a$CO$_2$R$^b$; C(=NH)NH$_2$; SO$_2$R$^c$; NR$^a$SO$_2$R$^c$; and CH(CF$_3$)NH$_2$;

R$^2$ represents a phenyl or heteroaryl group which is optionally substituted by one or more substituents independently selected from:
halogen atoms;
NR$^a$R$^b$;

$C_{1-4}$alkyl, $C_{1-4}$alkoxy, $C_{1-4}$alkoxy$C_{1-4}$alkyl, $C_{2-4}$alkenyl and $C_{2-4}$alkynyl groups, each optionally substituted by one or more substituents independently selected from halogen atoms and $NR^aR^b$ groups; and —$(CH_2)_p$—R' in which p is 0, 1, 2, 3 or 4 and R' represents one of the following substituents: OH; $NO_2$; CN; $COR^c$; $O.CO.R^c$; $CO_2R^b$; $NR^a.COR^c$; $NR^aCO_2R^b$; $C(=NH)NH_2$; $SO_2R^c$; $NR^aSO_2R^c$; and $CH(CF_3)NH_2$;

and/or which is optionally substituted on adjacent ring atoms by a group -$NR^a.CO.(CH_2)_n$— or —$(CH_2)_n.CO.NR^a$— forming a fused ring;

$R^a$ represents a hydrogen atom or a $C_{1-4}$alkyl group;

$R^b$ represents a hydrogen atom, a $C_{1-4}$alkyl group optionally substituted by a group $NR^aR^a$, or a cycloalkyl group in which a $CH_2$ moiety may be replaced by an oxygen atom or an $NR^a$ group;

$R^c$ represents a hydrogen atom, a group —$NR^aR^b$, or a $C_{1-4}$alkyl group optionally substituted by a group $NR^aR^b$;

or $R^a$ and $R^b$ together may, when attached to the same nitrogen atom, represent a —$(CH_2)_m$— group in which a $CH_2$ moiety may be replaced by an oxygen atom or an —$NR^a$-group;

m represents 4 or 5;

n represents 1 or 2; and each of $R^3$ and $R^4$ independently represents a hydrogen atom or a $C_{1-4}$alkyl group;

or a salt thereof.

2. A compound as claimed in claim 1, in which $R^1$ represents a pyrrolidine, morpholine, piperazine, piperidine, azetidine, thiomorpholine or homopiperazine ring.

3. A compound as claimed in claim 2, in which $R^1$ represents a pyrrolidine ring.

4. A compound according to claim 1, in which $R^1$ is unsubstituted or substituted by one or more substituents selected from halogen atoms; OH; =O; methyl; methoxy; trifluoromethyl;

trifluoromethoxy; CN; $NR^aR^b$; $COR^c$; $O.CO.R^c$; $CO_2R^a$; $NR^a.COR^c$; and $NR^aCO_2R^b$; in each of which each of $R^a$, $R^b$ and $R^c$ independently represents an alkyl group or a hydrogen atom, or $R^c$ may also represent an $NR^aR^b$ group.

5. A compound as claimed in claim 4, in which $R^1$ is unsubstituted or substituted by one or two fluorine atoms, a hydroxy group, a =O group, a methyl group or a $CO.NH_2$ group.

6. A compound according to claim 1, in which $R^2$ represents a pyridine, pyrazole, isoxazole, oxazole, imidazole, thioazole, 1,3,4-oxadiazole, 1,3,4-oxathiazole, pyrimidine or thiophene ring.

7. A compound according to claim 1, in which $R^2$ represents a pyridine, pyrazole, oxazole, isoxazole, thiazole or phenyl ring.

8. A compound according to claim 1, in which $R^2$ is unsubstituted or substituted by one or more substituents selected from halogen atoms; $NR^aR^b$; $C_{1-4}$alkyl optionally substituted by $NR^aR^b$; $C_{1-4}$alkoxy optionally substituted by $NR^aR^b$; -$CONR^aR^b$; $NR^aCOR^c$; or $SO_2R^c$; or in which $R^2$ is a group which is substituted on adjacent ring atoms by a group —$NR^a.CO.(CH_2)_n$— or —$(CH_2)_n.CO.NR^a$— forming a fused ring.

9. A compound as claimed in claim 8, in which $R^2$ is unsubstituted or substituted by one or more substituents selected from the following, where R" represents a hydrogen atom or a $C_{1-4}$alkyl group: R"; OR"; CO.NR"R"; NR".CO.R"; $SO_2R$"; 4-morpholine; NR".CO.1-pyrrolidine; 1-(4-R"piperazine); NR"$(CH_2)_2$N R"R"; CO.NR"; CO-1-(4-R"piperazine); CO.NR".4-(1- R"piperidine); and CO.NR". $(CH_2)_2$.N R" R"; or in which $R^2$ is a group which is substituted on adjacent ring atoms by a group —$NR^a.CO.(CH_2)_n$— or —$(CH_2)_n.CO.NR^a$— forming a fused ring.

10. A compound as claimed in claim 9, in which $R^2$ is unsubstituted or substituted by one or more substituents selected from Me; OMe; $CONH_2$; NH.CO.Me; NH.CO.$CH_2NMe_2$; $CO.NH_2$; $SO_2Me$; 4-morpholine; NH.CO.1-pyrrolidine; 1-(4-Me-piperazine); $NMe_2$; NMe.CO.Me; NH.$(CH_2)_2.NMe_2$; NMe.$(CH_2)_2.NMe_2$; C0.1-(4-Me-piperazine); CO.NH.4-(1-Me-piperidine); and CO.NH. $(CH_2)_2.NMe_2$; or in which $R^2$ represents:

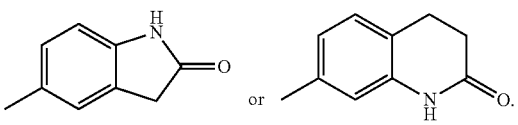

11. A compound according to claim 1, in which $R^2$ represents an optionally substituted heteroaryl group.

12. A compound according to claim 1, in which each of $R^3$ and $R^4$ independently represents a methyl group or a hydrogen atom.

13. A compound as claimed in claim 12, in which both of $R^3$ and $R^4$ are hydrogen atoms.

14. A compound according to claim 1, in which $R^a$ is a methyl group or a hydrogen atom; $R^b$ is a methyl group, a hydrogen atom, a group $(CH_2)_xNR^aR^a$ where x is 2, 3 or 4, or a piperidine group or $R^a$ and $R^b$ together represent —$(CH_2)_4$—, —$(CH_2)_5$—, —$(CH_2)_2.O.(CH_2)_2$— or —$(CH_2)_2.NR^b.(CH_2)_2$—; and $R^c$ represents a group $NR^aR^b$.

15. A compound as claimed in claim 1, in which $R^1$ represents a pyrrolidine ring which is unsubstituted or substituted by a hydroxy group or a $CO.NH_2$ group; $R^2$ represents a pyridine, pyrazole, oxazole, isoxazole, thioazole or phenyl ring which is unsubstituted or substituted by one or more substituents selected from —$NR^aR^b$, $C_{1-4}$alkoxy, —$NR^a.CO.R^c$, —$CO.NR^aR^b$, and $SO_2C_{1-4}$alkyl; or in which $R^2$ represents a pyridine, pyrazole, oxazole, isoxazole, thioazole or phenyl ring which is substituted on adjacent ring atoms by a group —$NR^a.CO.(CH_2)_n$— or —$(CH_2)_{n.CO.NR}{}^a$— forming a fused ring; and each of $R^3$ and $R^4$ represents a hydrogen atom.

16. A compound as claimed in claim 15, in which $R^1$ represents an unsubstituted pyrrolidine ring; $R^2$ represents a 2-Me-pyrazole, phenyl, or pyridyl ring which is mono-substituted by a substituent selected from —$NR^aR^b$, $C_{1-4}$alkoxy, —$NR^a.CO.R^c$, —$CO.NR^aR^b$, and $SO_2C_{1-4}$alkyl; or in which $R^2$ represents a phenyl or pyridyl ring, which is substituted on adjacent ring atoms by a group —$NR^a.CO.(CH_2)_n$— or —$(CH_2)_n.CO.NR^a$— forming a fused ring; and each of $R^3$ and $R^4$ represents a hydrogen atom.

17. A compound as claimed in claim 1, in which $R^1$ represents a morpholine, piperazine, piperidine, azetidine, thiomorpholine or homopiperazine ring, which is unsubstituted or substituted by a hydroxy group or a $CO.NH_2$ group; $R^2$ represents a pyridine, pyrazole, oxazole, isoxazole, thioazole or phenyl ring which is unsubstituted or substituted by one or more substituents selected from —$NR^aR^b$, $C_{1-4}$alkoxy, —$NR^a.CO.R^c$, —$CO.NR^aR^b$, and $SO_2C_{1-4}$alkyl; or in which $R^2$ represents a pyridine, pyrazole, oxazole, isoxazole, thioazole or phenyl ring which is substituted on adjacent ring atoms by a group —NR$^a$.CO.(CH$_2$)$_n$— or —(CH$_2$)$_n$.CO.NR$^a$— forming a fused ring; and each of R$^3$ and R$^4$ represents a hydrogen atom.

18. A compound as claimed in claim 16, in which R$^1$ represents an unsubstituted morpholine, piperazine, piperidine, azetidine, thiomorpholine or homopiperazine ring; R$^2$ represents a 2-Me-pyraxole, phenyl, or pyridyl ring which is mono-substituted by a substituent selected from —NR$^a$R$^b$, C$_{1-4}$alkoxy, —NR$^a$.CO.R$^c$, —CO.NR$^a$R$^b$, and SO$_2$C$_{i-4}$alkyl; or in which R$^2$ represents a phenyl or pyridyl ring, which is substituted on adjacent ring atoms by a group —NR$^a$.CO. (CH$_2$)$_n$— or —(CH$_2$)$_n$.CO.NR$^a$—forming a fused ring; and each of R$^3$ and R$^4$ represents a hydrogen atom.

19. A compound as claimed in claim 1, selected from:
    5-(2-Phenylamino-p yrimidin-4-yl)-2-pyrrolidin-1-yl-benzonitrile
    5-[2-(Pyridin-4-ylamino)-pyrimidin-4-yl]-2-pyrrolidin-1-yl-benzonitrile
    5-[2-(Pyridin-2-ylamino)-pyrimidin-4-yl]-2-pyrrolidin-1-yl-benzonitrile
    2-Pyrrolidin-1-yl-5-[2-(3 -trifluoromethyl-phenylamino)-pyrimidin-4- yl]-benzonitrile
    2-[4-(3-Cyano-4-pyrrolidin-l-yl-phenyl)-pyrimidin-2-ylamino]-oxazole-5-carboxylic acid amide
    5-[2-(5-Methyl-isoxazol-3-ylamino)-pyrimidin-4-yl]-2-pyrrolidin-1-yl-benzonitrile
    2-[4-(3-Cyano-4-pyrrolidin-1-yl-phenyl)-pyrimidin-2-ylamino]-oxazole-4-carboxylic acid amide
    5-[4-(3-Cyano-4-pyrrolidin-1-yl-phenyl)-pyrimidin-2-ylamino]-2-methyl-2H-pyrazole-3-carboxylic acid amide
    5-[2-(5-Methyl-thiazol-2-ylamino)-pyrimidin-4-yl]-2-pyrrolidin-1-yl-benzonitrile
    5-[2-(Oxazol-2-ylamino)-pyrimidin-4-yl]-2-pyrrolidin-1-yl-benzonitrile
    5-[2-(4-Methyl-thiazol-2-ylamino)-pyrimidin-4-yl]-2-pyrrolidin-1-yl-benzonitrile
    4-[4-(3-Cyano-4-pyrrolidin-1-yl-phenyl)-pyrimidin-2-ylamino]-3-methyl-benzamide
    5-[2-(3-Fluoro-phenylamino)-pyrimidin-4-yl]-2-pyrrolidin-1-yl-benzonitrile
    5-[2-(4-Fluoro-phenylamino)-pyrimidin-4-yl]-2-pyrrolidin-1-yl-benzonitrile
    5-[2-(3-Methoxy-phenylamino)-pyrimidin-4-yl]-2-pyrrolidin-1-yl-benzonitrile
    5-[2-(Pyridin-3-ylamino)-pyrimidin-4-yl]-2-pyrrolidin-1-yl-benzonitrile
    5-[2-(3-Methyl-isoxazol-5-ylamino)-pyrimidin-4-yl]-2-pyrrolidin-1-yl-benzonitrile
    5-[2-(2-Methyl-2H-pyrazol-3-ylamino)-pyrimidin-4-yl]-2-pyrrolidin-1-yl-benzonitrile
    5-[2-(1-Methyl-1H-pyrazol-3-ylamino)-pyrimidin-4-yl]-2-pyrrolidin-1-yl-benzonitrile
    N-{5-[4-(3-Cyano-4-morpholin-4-yl-phenyl)-pyrimidin-2-ylamino]-pyridin-2-yl}-acetamide
    N-(5-{4-[3Cyano-4-(4-methyl-piperazin-1-yl)-phenyl]-pyrimidin-2-ylamino}-pyridin-2-yl)-acetamide
    5-[4-(3-Cyano-4-pyrrolidin-1-yl-phenyl)-pyrimidin-2-ylamino]-1-methyl-1H-pyrazole-3-carboxylic acid amide
    1-{4-[2-(6-Acetylamino-pyridin-3-ylamino)-pyrimidin-4-yl]-2-cyano-phenyl}-piperidine-4-carboxylic acid amide
    (R)-1-{4-[2-(6-Acetylamino-pyridin-3-ylamino)-pyrimidin-4-yl]-2-cyano-phenyl }-pyrrolidine-2-carboxylic acid amide
    5-[2-(4-Methoxy-phenylamino)-pyrimidin-4-yl]-2-pyrrolidin-1-yl-benzonitrile
    3-[4-(3-Cyano-4-pyrrolidin-1-yl-phenyl)-pyrimidin-2-ylamino]-benzamide
    N-{3-[4-(3-Cyano-4-pyrrolidin-1-yl-phenyl)-pyrimidin-2-ylamino]-phenyl }-acetamide
    4-[4-(3-Cyano-4-pyrrolidin-1-yl-phenyl)-pyrimidin-2-ylamino]-benzamide
    N-{4-[4-(3-Cyano-4-pyrrolidin-l-yl-phenyl)-pyrimidin-2-ylamino]-phenyl}-acetamide
    5-[2-(3-Methanesulfonyl-phenylamino)-pyrimidin-4-yl]-2-pyrrolidin-1-yl-benzonitrile
    5-[2-(2-Oxo-2,3-dihydro-1H-indol-5-ylamino)-pyrimidin-4-yl]-2-pyrrolidin-1-yl-benzonitrile
    N-{5-[4-(3-Cyano-4-pyrrolidin-l-yl-phenyl)-pyrimidin-2-ylamino]-pyridin-2-yl}-acetamide
    5-[2-(6-Morpholin-4-yl-pyridin-3-ylamino)-pyrimidin-4-yl]-2-pyrrolidin-1-yl-benzonitrile 5-[2-(2-Oxo-1,2,3,4-tetrahydro-quinolin-7-ylamino)-pyrimidin-4-yl]-2-pyrrolidin-1-yl-benzonitrile
    Pyrrolidine-1-carboxylic acid {3-[4-(3-cyano-4-pyrrolidin-1-yl-phenyl)-pyrimidin-2-ylamino]-phenyl}-amide
    5-{2-[6-(4-Methyl-piperazin-1-yl)-pyridin-3-ylamino]-pyrimidin-4-yl}-2-pyrrolidin-1-yl-benzonitrile
    5-[2-(6-Dimethylamino-pyridin-3-ylamino)-pyrimidin-4-yl]-2-pyrrolidin-1-yl-benzonitrile
    N-{4-[4-(3-Cyano-4-pyrrolidin-1-yl-phenyl)-pyrimidin-2-ylamino]-phenyl}-N-methyl-acetamide
    N-(5-{4-[3-Cyano-4-(S)-(3-hydroxy-pyrrolidin-1-yl)-phenyl]-pyrimidin-2-ylamino }-pyridin-2-yl)-acetamide
    5-{2-[6-(2-Dimethylamino-ethylamino)-pyridin-3-ylamino]-pyrimidin-4-yl}-2-pyrrolidin-1-yl-benzonitrile
    5-(2-{6-[(2-Dimethylamino-ethyl)-methyl-amino]-pyridin-3-ylamino}-pyrimidin-4-yl)-2-pyrrolidin-1-yl-benzonitrile
    5-{2-[3-(4-Methyl-piperazine- 1-carbonyl)-phenylamino]-pyrimidin-4-yl}-2-pyrrolidin-1-yl-benzonitrile
    3-[4-(3-Cyano-4-pyrrolidin-1-yl-phenyl)-pyrimidin-2-ylamino]-N-(1-methyl-piperidin-4-yl)-benzamide
    3-[4-(3-Cyano-4-pyrrolidin-1-yl-phenyl)-pyrimidin-2-ylamino]-N-(2-dimethylamino-ethyl)-benzamide
    2-((S)-3-Hydroxy-pyrrolidin-1-yl)-5-[2-(2-methyl-2H-pyrazol-3-ylamino)-pyrimidin-4-yl]-benzonitrile
    (R)-1-{2-Cyano-4-[2-(2-methyl-2H-pyrazol-3-ylamino)-pyrimidin-4-yl]-phenyl}-pyrrolidine-2-carboxylic acid amide
    N-{5-[4-(3-Cyano-4-pyrrolidin-1-yl-phenyl)-pyrimidin-2-ylamino]-pyridin-2-yl}-2-dimethylamino-acetamide
    2-((S)-3-Hydroxy-pyrrolidin-1-yl)-5-{2-[6-(4-methyl-piperazin-1 -yl)-pyridin-3-ylamino]-pyrimidin-4-yl}-benzonitrile
    (R)-1-(2-Cyano-4-{2-[6-(4-methyl-piperazin-1-yl)-pyridin-3-ylamino]-pyrimidin-4-yl}-phenyl)-pyrrolidine-2-carboxylic acid amide;

or a salt thereof.

20. A process for the preparation of a compound as claimed in claim 1, which comprises either:

(a) reacting a compound of the general formula II:

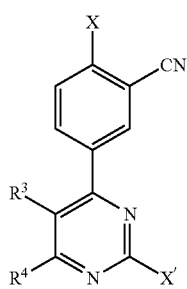

with amines of the general formula $R^2NH_2$ and $R^1H$; or
(b) reacting a compound of formula III

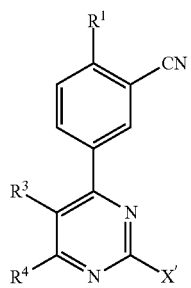

with a compound of the general formula $R^2NH_2$; or
(c) reacting a compound of formula IV

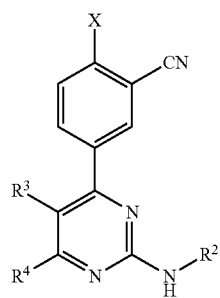

with a compound of the general formula $R^1H$;

in which X represents a leaving group, X' represents a leaving group, and $R^1$ and $R^2$ have the meanings given in any one of the preceding claims.

21. A pharmaceutical composition which comprises a compound as claimed in claim 1, together with a pharmaceutically suitable carrier, and optionally also containing an additional active ingredient.

* * * * *